(12) United States Patent
Iguchi et al.

(10) Patent No.: US 8,624,017 B2
(45) Date of Patent: Jan. 7, 2014

(54) PROBE, POLYMORPHISM DETECTION METHOD, METHOD OF EVALUATING DRUG EFFICACY OR TOLERANCE, DISEASE PREDICTION METHOD AND REAGENT KIT

(75) Inventors: Aki Iguchi, Kyoto (JP); Kaoru Kurose, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 13/458,706

(22) Filed: Apr. 27, 2012

(65) Prior Publication Data
US 2012/0282607 A1    Nov. 8, 2012

(30) Foreign Application Priority Data

May 2, 2011 (JP) ................................. 2011-102987
Mar. 30, 2012 (JP) ................................. 2012-082390

(51) Int. Cl.
*C07H 21/04* (2006.01)
*C12Q 1/68* (2006.01)

(52) U.S. Cl.
USPC ...................................... 536/24.31; 435/6.11

(58) Field of Classification Search
None
See application file for complete search history.

(56) References Cited

U.S. PATENT DOCUMENTS

| 2002/0106653 A1 | 8/2002 | Kurane et al. |
| 2006/0057579 A1 | 3/2006 | Kotani et al. |
| 2008/0311579 A1 | 12/2008 | French et al. |

FOREIGN PATENT DOCUMENTS

| EP | 2224017 A1 | 9/2010 |
| JP | 2002-119291 A | 4/2002 |
| JP | 4454366 B | 4/2010 |
| WO | 02/052044 A2 | 7/2002 |
| WO | 2009/105680 A2 | 8/2009 |

OTHER PUBLICATIONS

Kondo et al., Pharmaceutical Research, 2004, vol. 21, pp. 1895-1903.*
Buck et al., BioTechniques, 1999, vol. 27, pp. 528-536.*
Housni et al., Clinical Chemstry, 2003, vol. 49, pp. 1669-1672.*
Behrens et al., System. Appl. Microbiol., 2004, vol. 27, pp. 565-572.*
Crockett et al., "Fluorescein-Labeled Oligonucleotides for Real-Time PCR: Using the Inherent Quenching of Deoxyguanosine Nucleotides," Analytical Biochemistry, 290: 89-97 (2001).
Extended European Search Report issued in corresponding European Patent Application No. 12166068.2 dated Aug. 7, 2012.
Ozawa et al. "Polymorphisms in the ABCC2 (CMOAT/MRP2) Gene Found in 72 Established Cell Lines Derived From Japanese Individuals: An Association Between Single Nucleotide Polymorphisms in the 5'-Untranslated Region and Exon 28." Drug Metabolism and Disposition, 30: 363-364 (2002).
Kobayashi et al, "Functional Assessment of ABCG2 (BCRP) Gene Polymorphisms to Protein Expression in Human Placenta." Drug Metabolism and Disposition, 33: 94-101 (2005).
Matsuo et al. "Common defects of ABCG2, a high-capacity urate exporter, cause gout" Experimental Medicine, 28: 1285-1269 (2010).
Taheri et al. "Effect of MDR1 polymorphism on multidrug resistance expression in breast cancer patients." Genetics and Molecular Research, 9: 34-40 (2010).

* cited by examiner

*Primary Examiner* — Anne Gussow
*Assistant Examiner* — Mindy G Brown
(74) *Attorney, Agent, or Firm* — Morgan, Lewis & Bockius LLP

(57) ABSTRACT

A probe for detecting polymorphism in the ABCG2 gene is constituted by including, for example, an oligonucleotide which is complementary to a base sequence including the 301st to the 311th bases of the base sequence indicated in SEQ ID NO:1 and having a length of from 11 bases to 50 bases, and has an identity of at least 80%, and in which a base corresponding to the 311th base has been labeled with a fluorescent dye.

11 Claims, 11 Drawing Sheets

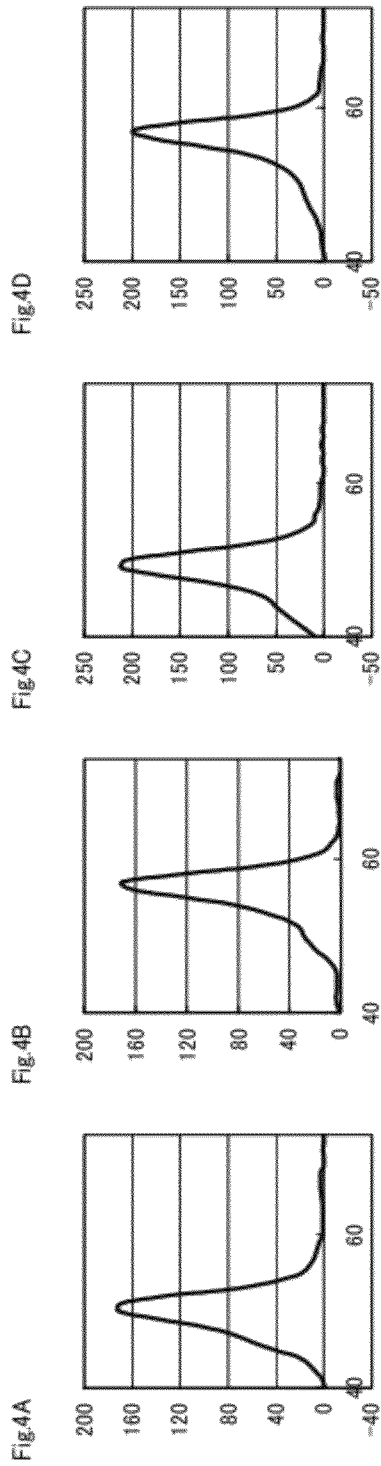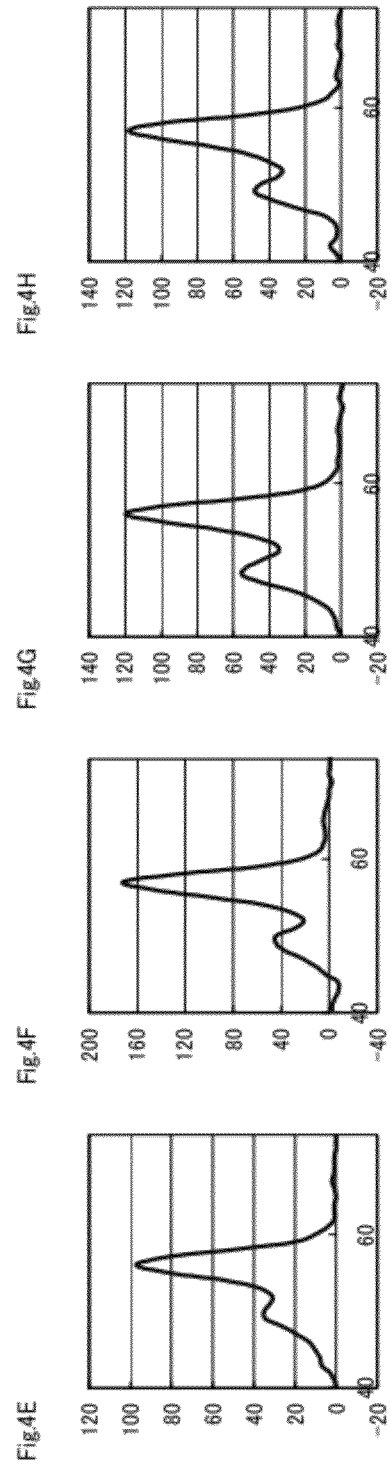

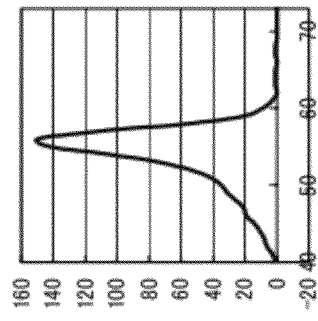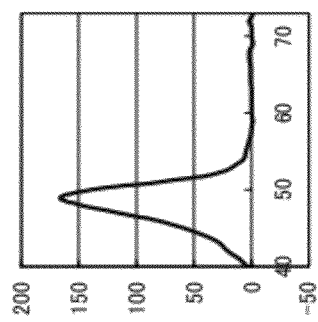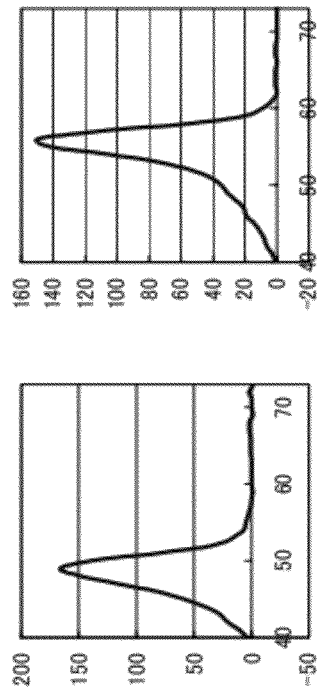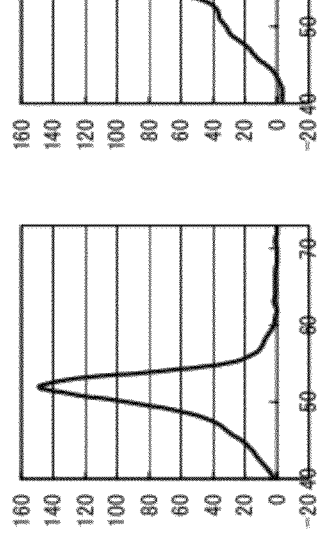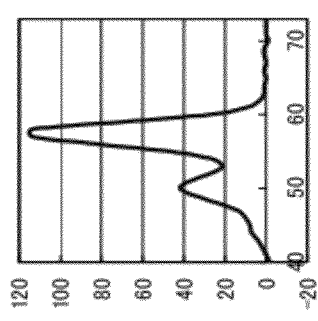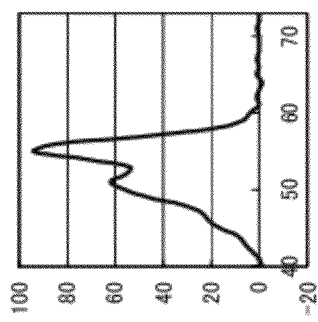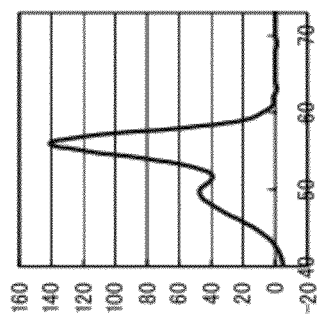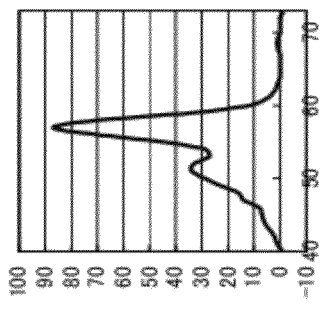

PROBE, POLYMORPHISM DETECTION METHOD, METHOD OF EVALUATING DRUG EFFICACY OR TOLERANCE, DISEASE PREDICTION METHOD AND REAGENT KIT

This application claims priority from Japanese Patent Application No. 2011-102987 filed on May 2, 2011 and Japanese Patent Application No. 2012-082390 filed on Mar. 30, 2012, which are incorporated by reference herein in its entirety.

Sequence Listing Submission via EFS-Web

A computer readable text file, entitled "SequenceListing.txt," created on or about Apr. 26, 2012 with a file size of about 9 kb contains the sequence listing for this application and is hereby incorporated by reference in its entirety.

All documents, patent applications and technical standards mentioned in the present specification are incorporated herein by reference to the same extent as if each individual document, patent application or technical standard is specifically and individually indicated to be incorporated by reference.

BACKGROUND

1. Technical Field

The present invention relates to a probe for detecting polymorphism, a method of detecting polymorphism, a method of evaluating a drug efficacy or tolerance, a disease prediction method, and a reagent kit for detecting polymorphism.

2. Related Art

So far, Urate Transporter (URAT1/SLC22A12), which is a uric acid reabsorption transporter, and Glucose Transporter 9 (GLIT9/SLC22A12) have been known as therapeutic target molecules for hyperuricemia.

In recent years, it has been proved that the ABCG2 (ATP-binding cassette sub-family G member 2) gene, which is also referred to as BCRP (breast cancer resistance protein), codes for a high volume urination transporter.

It has also been suggested that the presence of polymorphism in the ABCG2 gene is linked to an increased risk of developing gout, and it has been proved that the ABCG2 gene is a causative gene of gout (see, for example, JIKKEN IGAKU (Experimental Medicine), 2010, Vol. 28, No. 8, pp. 1285-1289).

Further, it has been suggested that the presence of polymorphism in the ABCG2 gene is relevant to abnormal protein expression in a placenta (see, for example, Drug. Metab. Dispos., 2005, Vol. 33, No. 1, pp. 94-101), and a method, in which polymorphism in the ABCG2 gene may be measured in a short time, at a low cost and easily, is demanded.

As a method of measuring polymorphism of a gene, a PCR-RFLP method is known. In this method, PCR is carried out using primers that have been designed so as to amplify a region containing bases that are desired to be measured; the products obtained by the amplification are subjected to cleaving with a restriction enzyme, that is selected so that the presence or absence of the cleaving by the restriction enzyme depends on whether the mutation of the particular base exists or not; and then, the resultant is electrophoresed to detect whether the products obtained by the amplification have been cleaved or not (see, for example, Genet. Mol. Res., 2010, Vol. 9, No. 1, pp. 34-40).

In addition, a method, in which a region containing a mutation is amplified by a PCR method; thereafter, melting curve analysis is carried out using a nucleic acid probe that has been labeled with a fluorescent dye; and, based on the results of the melting curve analysis, the mutation in the base sequence is analyzed, is also known (see, for example, Japanese Patent Application Laid-Open (JP-A) No. 2002-119291).

However, in the PCR-RFLP method, it is necessary to carry out a PCR reaction, and thereafter collect the amplification products, and treat them with a restriction enzyme. Therefore, there may be a risk that the amplification products may contaminate the following reaction system, and this may cause a false-positive or false-negative result. In addition, since the restriction enzyme treatment is carried out after the completion of PCR and then the resultant is electrophoresed, it may take a very long time until the detection. Furthermore, this method is hard to automate due to complex operations thereof.

Therefore, it has been demanded to further develop a technique for detecting polymorphism in the ABCG2 gene.

SUMMARY OF THE INVENTION

Problems to be Solved by the Invention

An object of the present invention is to provide a probe for detecting polymorphism which may make it possible to detect polymorphism in the ABCG2 gene with a high sensitivity and easily, and a method of detecting polymorphism by using the probe. Another object of the present invention is to provide a method of evaluating a drug efficacy or tolerance by using the detection method, and a disease prediction method in which the detection method is used. Yet another object of the present invention is to provide a reagent kit for detecting polymorphism by using the detection probe.

Means for Solving the Problems

Concrete means for solving the problems are as follows.
<1> A probe for detecting polymorphism in the ABCG2 gene, the probe including at least one fluorescently labeled oligonucleotide selected from the group consisting of a P1 fluorescently labeled oligonucleotide, a P1' fluorescently labeled oligonucleotide, a P2 fluorescently labeled oligonucleotide, a P2' fluorescently labeled oligonucleotide, a P3 fluorescently labeled oligonucleotide and a P3' fluorescently labeled oligonucleotide;

the P1 fluorescently labeled oligonucleotide having a sequence that is complementary to a base sequence including the 301st to the 311th bases of the base sequence indicated in SEQ ID NO:1 and having a length of from 11 bases to 50 bases, the sequence having an identity of at least 80% with respect to a sequence that is complementary to SEQ ID NO:1 with the exception that its base corresponding to the 311th base is a guanine, and the base corresponding to the 311th base being labeled with a fluorescent dye, the P1' fluorescently labeled oligonucleotide having a sequence including the 301st to 311th bases of the sequence indicated in SEQ ID NO:1 and having a length of from 11 bases to 50 bases, the sequence being hybridized under stringent conditions with respect to a complementary strand of a base sequence having the same bases as SEQ ID NO:1 with the exception that the base corresponding to the 311th base in SEQ ID NO:1 is a guanine, and the base corresponding to the 311th base in SEQ ID NO:1 being labeled with a fluorescent dye, the P2 fluorescently labeled oligonucleotide having a sequence that is complementary to a base sequence including the 234th to the 251st bases of the base sequence indicated in SEQ ID NO:2 and having a length of from 18 bases to 50 bases, the sequence having an identity of at least 80% with respect to a sequence that is complementary to SEQ ID NO:2 with the exception that its base corresponding to the 251st base is a guanine, and the base corresponding to the 251st base being labeled with a fluorescent dye, the P2' fluorescently labeled oligonucleotide having a sequence including the 234th to 251th bases of the sequence indicated in SEQ ID NO:2 and having a length of from 18 bases to 50 bases, the sequence being hybridized under stringent conditions with respect to a complementary strand of a base sequence having the same bases as SEQ ID NO:2 with the exception that the base corresponding to the 251th base in SEQ ID NO:2 is a guanine, and the base corresponding to the 251th base in SEQ ID NO:2 being labeled with a fluorescent dye, the P3 fluorescently labeled oligonucleotide having a sequence that is complementary to a base sequence including the 152nd to the 161st bases of the base sequence indicated in SEQ ID NO:3 and having a length of from 10 bases to 50 bases, the sequence having an identity of at least 80% with respect to a sequence that is complementary to SEQ ID NO:3 with the exception that its base corresponding to the 152nd base is a guanine, and the base corresponding to the 152nd base being labeled with a fluorescent dye, and the P3' fluorescently labeled oligonucleotide having a sequence including the 152nd to 161st bases of the sequence indicated in SEQ ID NO:3 and having a length of from 10 bases to 50 bases, the sequence being hybridized under stringent conditions with respect to a complementary strand of a base sequence having the same bases as SEQ ID NO:3 with the exception that the base corresponding to the 152nd base in SEQ ID NO:3 is a guanine, and the base corresponding to the 152nd base in SEQ ID NO:3 being labeled with a fluorescent dye.

<2> The probe for detecting polymorphism of <1>, wherein the base in the P1 fluorescently labeled oligonucleotide corresponding to the 311th base and labeled with the fluorescent dye is at a position of any one of 1st to 3rd positions from a 5' end; the base in the P1' fluorescently labeled oligonucleotide corresponding to the 311th base and labeled with the fluorescent dye is at a position of any one of 1st to 3rd positions from a 5' end; the base in the P2 fluorescently labeled oligonucleotide corresponding to the 251st base and labeled with the fluorescent dye is at a position of any one of 1st to 3rd positions from a 5' end; the base in the P2' fluorescently labeled oligonucleotide corresponding to the 251st base and labeled with the fluorescent dye is at a position of any one of 1st to 3rd positions from a 5' end; the base in the P3 fluorescently labeled oligonucleotide corresponding to the 152nd base and labeled with the fluorescent dye is at a position of any one of 1st to 3rd positions from a 3' end; and the base in the P3' fluorescently labeled oligonucleotide corresponding to the 152nd base and labeled with the fluorescent dye is at a position of any one of 1st to 3rd positions from a 3' end.

<3> The probe for detecting polymorphism in the ABCG2 gene of <1> or <2>, wherein the base in the P1 fluorescently labeled oligonucleotide corresponding to the 311th base and labeled with the fluorescent dye is at a 5' end; the base in the P1' fluorescently labeled oligonucleotide corresponding to the 311th base and labeled with the fluorescent dye is at a 5' end; the base in the P2 fluorescently labeled oligonucleotide corresponding to the 251st base and labeled with the fluorescent dye is at a 5' end; the base in the P2' fluorescently labeled oligonucleotide corresponding to the 251st base and labeled with the fluorescent dye is at a 5' end; the base in the P3 fluorescently labeled oligonucleotide corresponding to the 152nd base and labeled with the fluorescent dye is at a 3' end; and the base in the P3' fluorescently labeled oligonucleotide corresponding to the 152nd base and labeled with the fluorescent dye is at a 3' end.

<4> The probe for detecting polymorphism of any one of <1> to <3>, wherein a fluorescence intensity at the time when the fluorescently labeled oligonucleotide is hybridized to its target sequence is decreased or increased as compared to the fluorescence intensity at the time when the fluorescently labeled oligonucleotide is not hybridized to its target sequence.

<5> The probe for detecting polymorphism of any one of <1> to <4>, wherein a fluorescence intensity at the time when the fluorescently labeled oligonucleotide is hybridized to its target sequence is decreased as compared to the fluorescence intensity at the time when the fluorescently labeled oligonucleotide is not hybridized to its target sequence.

<6> The probe for detecting polymorphism of any one of <1> to <5>, wherein the P1 fluorescently labeled oligonucleotide has a length of from 11 bases to 40 bases; the P1' fluorescently labeled oligonucleotide has a length of from 11 bases to 40 bases; the P2 fluorescently labeled oligonucleotide has a length of from 18 bases to 40 bases; the P2' fluorescently labeled oligonucleotide has a length of from 18 bases to 40 bases; the P3 fluorescently labeled oligonucleotide has a length of from 10 bases to 40 bases; and the P3' fluorescently labeled oligonucleotide has a length of from 10 bases to 40 bases.

<7> The probe for detecting polymorphism of any one of <1> to <6>, wherein the P1 fluorescently labeled oligonucleotide has a length of from 11 bases to 28 bases; the P1' fluorescently labeled oligonucleotide has a length of from 11 bases to 28 bases; the P2 fluorescently labeled oligonucleotide has a length of from 20 bases to 30 bases; the P2' fluorescently labeled oligonucleotide has a length of from 20 bases to 30 bases; the P3 fluorescently labeled oligonucleotide has a length of from 15 bases to 30 bases; and the P3' fluorescently labeled oligonucleotide has a length of from 15 bases to 30 bases.

<8> The probe for detecting polymorphism of any one of <1> to <7>, wherein the P1 fluorescently labeled oligonucleotide has a length of from 14 bases to 18 bases; the P1' fluorescently labeled oligonucleotide has a length of from 14 bases to 18 bases; the P2 fluorescently labeled oligonucleotide has a length of from 22 bases to 26 bases; the P2' fluorescently labeled oligonucleotide has a length of from 22 bases to 26 bases; the P3 fluorescently labeled oligonucleotide has a length of from 18 bases to 22 bases; and the P3' fluorescently labeled oligonucleotide has a length of from 18 bases to 22 bases.

<9> The probe for detecting polymorphism of any one of <1> to <8>, being a probe for melting curve analysis.

<10> A method of detecting a polymorphism in the ABCG2 gene, in which the probe for detecting a polymorphism of any one of <1> to <9> is used.

<11> The method of detecting polymorphism of <10>, in which at least two probes for detecting polymorphism selected from the group consisting of the P1 fluorescently labeled oligonucleotide, the P1' fluorescently labeled oligonucleotide, the P2 fluorescently labeled oligonucleotide, the P2' fluorescently labeled oligonucleotide, the P3 fluorescently labeled oligonucleotide and the P3' fluorescently labeled oligonucleotide of any one of <1> to <9> are used.

<12> The method of detecting polymorphism of <10> or <11>, which includes (I) contacting the probe for detecting polymorphism of any one of <1> to <9> and a single-stranded nucleic acid in a sample and hybridizing the fluorescently labeled oligonucleotide and the single-stranded nucleic acid to obtain a hybrid; (II) dissociating the hybrid by changing a temperature of the sample containing the hybrid, and measuring a change in a fluorescence signal caused by the dissociation of the hybrid; (III) measuring, based on the change in the fluorescence signal, a Tm value which is a temperature at which the hybrid dissociates; and (IV) detecting, based on the Tm value, whether polymorphism in the ABCG2 gene on the single-stranded nucleic acid in the sample exists or not.

<13> The method of detecting polymorphism of <12>, which further includes amplifying the nucleic acid before or simultaneously with the obtaining of the hybrid in (I).

<14> A method of evaluating a drug efficacy or tolerance, which includes detecting polymorphism in the ABCG2 gene by the method of detecting polymorphism of any one of <10> to <13>, and evaluating tolerance to the drug or the efficacy of the drug based on the presence or absence of detected polymorphism.

<15> A disease prediction method, which includes detecting polymorphism in the ABCG2 gene by the method of detecting polymorphism of any one of <10> to <13>, and predicting an incidence risk of a disease based on the presence or absence of detected polymorphism.

<16> A reagent kit, which contains the probe for detecting polymorphism of any one of <1> to <9>.

<17> The reagent kit of <16>, which further contains at least one primer set selected from the group consisting of: a primer set for amplifying a region containing a sequence in the base sequence indicated in SEQ ID NO:1 to which the P1 fluorescently labeled oligonucleotide may hybridize; a primer set for amplifying a region containing a sequence in the base sequence indicated in SEQ ID NO:1 to which the P1' fluorescently labeled oligonucleotide may hybridize; a primer set for amplifying a region containing a sequence in the base sequence indicated in SEQ ID NO:2 to which the P2 fluorescently labeled oligonucleotide may hybridize; a primer set for amplifying a region containing a sequence in the base sequence indicated in SEQ ID NO:2 to which the P2' fluorescently labeled oligonucleotide may hybridize; a primer set for amplifying a region containing a sequence in the base sequence indicated in SEQ ID NO:3 to which the P3 fluorescently labeled oligonucleotide may hybridize; and a primer set for amplifying a region containing a sequence in the base sequence indicated in SEQ ID NO:3 to which the P3' fluorescently labeled oligonucleotide may hybridize.

Effects of the Invention

According to the present invention, a probe for detecting polymorphism which may make it possible to detect polymorphism in the ABCG2 gene with a high sensitivity and easily, and a method of detecting polymorphism by using the probe may be provided. In addition, according to the present invention, a method of evaluating a drug efficacy or tolerance by using the detection method, and a disease prediction method in which the detection method is used may be provided. Further, according to the present invention, a reagent kit for detecting polymorphism by using the detection probe may be provided.

BRIEF DESCRIPTION OF THE DRAWINGS

FIG. 4A is melting curves obtained by using the polymorphism detection probe according to Example 2 of the present invention.

FIG. 4B is melting curves obtained by using the polymorphism detection probe according to Example 2 of the present invention.

FIG. 4C is melting curves obtained by using the polymorphism detection probe according to Example 2 of the present invention.

FIG. 4D is melting curves obtained by using the polymorphism detection probe according to Example 2 of the present invention.

FIG. 4E is melting curves obtained by using the polymorphism detection probe according to Example 2 of the present invention.

FIG. 4F is melting curves obtained by using the polymorphism detection probe according to Example 2 of the present invention.

FIG. 4G is melting curves obtained by using the polymorphism detection probe according to Example 2 of the present invention.

FIG. 4H is melting curves obtained by using the polymorphism detection probe according to Example 2 of the present invention.

FIG. 10A is melting curves obtained by using the polymorphism detection probe according to Comparative Example 2 of the present invention.

FIG. 10B is melting curves obtained by using the polymorphism detection probe according to Comparative Example 2 of the present invention.

FIG. 10C is melting curves obtained by using the polymorphism detection probe according to Comparative Example 2 of the present invention.

FIG. 10D is melting curves obtained by using the polymorphism detection probe according to Comparative Example 2 of the present invention.

FIG. 10E is melting curves obtained by using the polymorphism detection probe according to Comparative Example 2 of the present invention.

FIG. 10F is melting curves obtained by using the polymorphism detection probe according to Comparative Example 2 of the present invention.

FIG. 10G is melting curves obtained by using the polymorphism detection probe according to Comparative Example 2 of the present invention.

FIG. 10H is melting curves obtained by using the polymorphism detection probe according to Comparative Example 2 of the present invention.

DETAILED DESCRIPTION OF THE INVENTION

Mode for Carrying Out the Invention

Figure 1A:
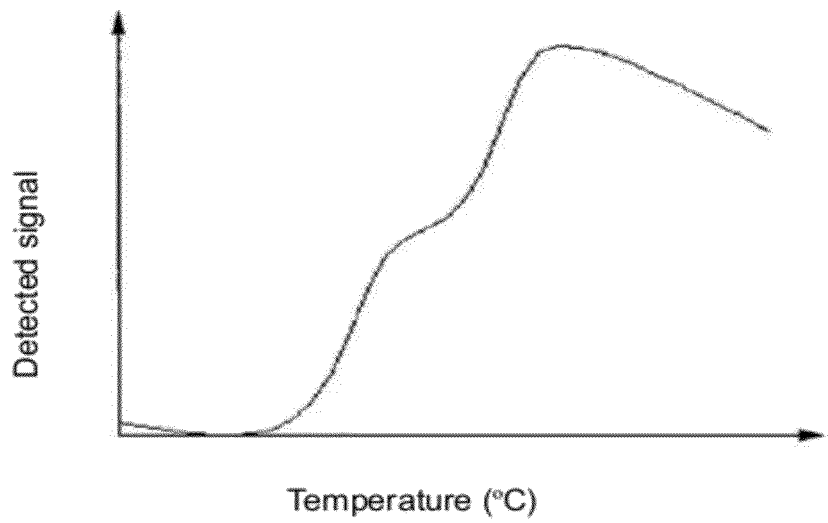
FIG. 1A is an example of a melting curve of a nucleic acid mixture.
Figure 1B:
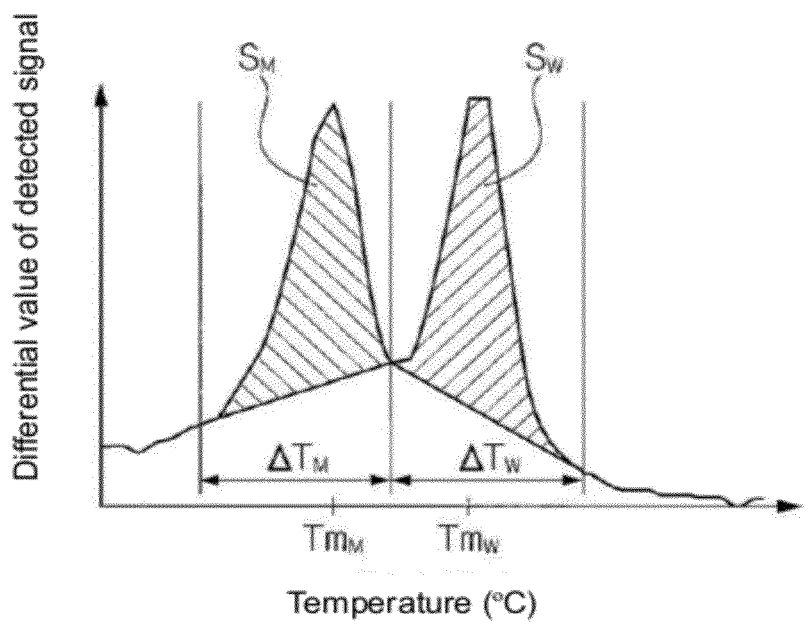
FIG. 1B is an example of a differential melting curve of a nucleic acid mixture.

The probe of the present invention is a probe for detecting polymorphism in the ABCG2 gene, the probe including at least one fluorescently labeled oligonucleotide selected from the group consisting of a P1 fluorescently labeled oligonucleotide, a P1' fluorescently labeled oligonucleotide, a P2 fluorescently labeled oligonucleotide, a P2' fluorescently labeled oligonucleotide, a P3 fluorescently labeled oligonucleotide and a P3' fluorescently labeled oligonucleotide.

According to the present invention, polymorphism in the ABCG2 gene may be detected with a high sensitivity and easily.

The base sequence of the ABCG2 gene is a sequence that corresponds to the 89011415th to the 89080010th bases of the sequence of Gene ID: 9429 and GenBank Accession No. 000004 (version: 000004.11). In the present specification, the sequence corresponding the 89011415th to the 89080010th bases is referred to as "the base sequence of the ABCG2 gene."

In the present invention, the descriptions of the base sequences of the sample nucleic acid in a sample to be detected and the probe or primer shall also apply to complementary base sequences thereof, respectively, unless otherwise specified. Further, when the description of a particular base sequence is applied to a complementary base sequence thereof, descriptions of base sequences recognized by the particular base sequence in the present invention should be applied provided that the recognition by the particular base sequence should be replaced with recognition by a complementary base sequence of the particular base sequence, within a range of the common general technical knowledge of those skilled in the art.

In the present invention, the term "Tm value" is defined as a temperature at which a double-stranded nucleic acid dissociates (dissociation temperature: Tm), and is generally defined as a temperature at which the absorbance at 260 nm has increased by 50% of the total increase in absorbance resulting from complete dissociation of the double-stranded nucleic acid. More specifically, when a solution containing a double-stranded nucleic acid such as a double-stranded DNA is heated, the absorbance at 260 nm of the double-stranded nucleic acid gradually increases. This is because the hydrogen bonds between both strands of the double-stranded DNA are broken by heating, thereby dissociating the double-stranded DNA into single-stranded DNAs (melting of DNA). When the double-stranded DNA has completely dissociated into single-stranded DNAs, the single-stranded DNAs exhibit an absorbance that is about 1.5 times the absorbance at the time of the initiation of the heating (i.e., the absorbance when the entire DNA is in the form of a double-stranded DNA), which serves as an indicator of the completion of the melting. The Tm value is defined based on this phenomenon. Tm values are defined based on such phenomena. The Tm values in the present invention mean temperatures at which the absorbance reaches 50% of the total increase between the initial absorbance and the final absorbance, unless otherwise noted.

In the present invention, when the phrase "the first to third bases from the 3' end" is used in connection to an oligonucleotide sequence, it is assumed that the base at the 3' end of the oligonucleotide chain is the first base from the 3' end. Similarly, when the phrase "1st to 3rd positions from the 5' end" is used, the 5' end of the oligonucleotide chain is considered to be the 1st position thereof.

In the present specification, the scope of the term "process" includes not only a discrete process, but also a process that cannot be clearly distinguished from another process as long as the expected effect of the process of interest is achieved.

In the present specification, any numerical range expressed using "to" refers to a range including the numerical values before and after "to" as the minimum and maximum values, respectively.

In a case in which the amount of a component that may be included in the composition is indicated in the present invention, when there are plural substances corresponding to the component in the composition, the indicated amount means the total amount of the plural substances present in the composition, unless specifically stated otherwise.

The present invention is described below.

<Probe for Detecting Polymorphism>

The probe for detecting polymorphism (hereinafter also simply referred to as "the probe") of the present invention includes at least one fluorescently labeled oligonucleotide selected from the group consisting of a P1 fluorescently labeled oligonucleotide, a P1' fluorescently labeled oligonucleotide, a P2 fluorescently labeled oligonucleotide, a P2' fluorescently labeled oligonucleotide, a P3 fluorescently labeled oligonucleotide and a P3' fluorescently labeled oligonucleotide as described below (hereinafter also simply referred to as "the fluorescently labeled oligonucleotide").

The P1 fluorescently labeled oligonucleotide is an oligonucleotide having a sequence that is complementary to a base sequence including the 301st to the 311th bases of the base sequence indicated in SEQ ID NO:1 and having a length of from 11 bases to 50 bases, the sequence having an identity of at least 80% with respect to a sequence that is complementary to SEQ ID NO:1 with the exception that its base corresponding to the 311th base is a guanine, and the base corresponding to the 311th base being labeled with a fluorescent dye;

the P1' fluorescently labeled oligonucleotide having a sequence including the 301st to 311th bases of the sequence indicated in SEQ ID NO:1 and having a length of from 11 bases to 50 bases, the sequence being hybridized under stringent conditions with respect to a complementary strand of a base sequence having the same bases as SEQ ID NO:1 with the exception that the base corresponding to the 311th base in SEQ ID NO:1 is a guanine, and the base corresponding to the 311th base in SEQ ID NO:1 being labeled with a fluorescent dye, the P2 fluorescently labeled oligonucleotide having a sequence that is complementary to a base sequence including the 234th to the 251st bases of the base sequence indicated in SEQ ID NO:2 and having a length of from 18 bases to 50 bases, the sequence having an identity of at least 80% with respect to a sequence that is complementary to SEQ ID NO:2 with the exception that its base corresponding to the 251st base is a guanine, and the base corresponding to the 251st base being labeled with a fluorescent dye, the P2' fluorescently labeled oligonucleotide having a sequence including the 234th to 251th bases of the sequence indicated in SEQ ID NO:2 and having a length of from 18 bases to 50 bases, the sequence being hybridized under stringent conditions with respect to a complementary strand of a base sequence having the same bases as SEQ ID NO:2 with the exception that the base corresponding to the 251th base in SEQ ID NO:2 is a guanine, and the base corresponding to the 251th base in SEQ ID NO:2 being labeled with a fluorescent dye, the P3 fluorescently labeled oligonucleotide having a sequence that is complementary to a base sequence including the 152nd to the 161st bases of the base sequence indicated in SEQ ID NO:3 and having a length of from 10 bases to 50 bases, the sequence having an identity of at least 80% with respect to a sequence that is complementary to SEQ ID NO:3 with the exception that its base corresponding to the 152nd base is a guanine, and the base corresponding to the 152nd base being labeled with a fluorescent dye, and the P3' fluorescently labeled oligonucleotide having a sequence including the 152nd to 161st bases of the sequence indicated in SEQ ID NO:3 and having a length of from 10 bases to 50 bases, the sequence being hybridized under stringent conditions with respect to a complementary strand of a base sequence having the same bases as SEQ ID NO:3 with the exception that the base corresponding to the 152nd base in SEQ ID NO:3 is a guanine, and the base corresponding to the 152nd base in SEQ ID NO:3 being labeled with a fluorescent dye.

The inclusion of at least one of such particular fluorescently labeled oligonucleotides may make it possible to detect polymorphism in the ABCG2 gene with a high sensitivity and easily.

The base sequence indicated in SEQ ID NO:1 is a part of the base sequence of the ABCG2 gene, and corresponds to 601 bases which are the 18597th to the 19196th bases in the 1st to the 68595th bases of the ABCG2 gene.

In the wild type of the ABCG2 gene, a base corresponding to the 301st base of the base sequence indicated in SEQ ID NO:1 is a G (guanine); but, in a mutant type thereof, the G has been mutated into an A (adenine).

In addition, in the wild type of the ABCG2 gene, the 12th amino acid in the amino acid sequence of the ABCG2 transporter is a valine (Val); but, in a mutant type of the ABCG2 gene, the amino acid is a methionine (Met) (this mutation is hereinafter referred to as "the V12M mutation").

In the P1 or P1' fluorescently labeled oligonucleotide, a "base corresponding to the 311th base" is a C (cytosine) that is a base complementary to a G (guanine) of the 311th base of the base sequence indicated in SEQ ID NO:1.

In the P1 or P1' fluorescently labeled oligonucleotide, this complementary base C, which has been fluorescently labeled, may exist at a position of any one of 1st to 3rd positions from the 5' end of the oligonucleotide. Alternatively, the base may exist at the 5' end of the oligonucleotide. Thereby, for example, the sensitivity for detecting polymorphism may be further improved. In addition, the P1 or P1' fluorescently labeled oligonucleotide may be obtained with a good productivity.

The P1 or P1' fluorescently labeled oligonucleotide is a probe that is capable of detecting polymorphism of the 301st base of the base sequence indicated in SEQ ID NO:1. This base is a G in a wild type and an A in a mutant type.

The P1 or P1' fluorescently labeled oligonucleotide needs to have a length of from 11 bases to 50 bases. When the base length is a length of 10 bases or less or a length of 51 bases or more, the sensitivity for detecting polymorphism in the ABCG2 gene may be decreased. From the view point of the sensitivity for detecting polymorphism, the base length of the P1 or P1' fluorescently labeled oligonucleotide may be a length of from 11 bases to 40 bases, a length of from 11 bases to 28 bases, or a length of from 14 bases to 18 bases.

By varying the base length of the P1 or P1' fluorescently labeled oligonucleotide, for example, the Tm value, which is a dissociation temperature of a hybrid formed by the P1 or P1' fluorescently labeled oligonucleotide and its complementary strand (target sequence), may be adjusted to a desired value.

The P1 fluorescently labeled oligonucleotide of the present invention has a homology with respect to a sequence that is complementary to the base sequence indicated in SEQ ID NO:1 with the exception that its base corresponding to the 311th base is a guanine.

More specifically, the P1 fluorescently labeled oligonucleotide of the present invention has an identity of not less than 80% with respect to a base sequence complementary to the base sequence indicated in SEQ ID NO:1.

In addition, from the view point of the detection sensitivity, the P1 fluorescently labeled oligonucleotide may have an identity of not less than 85%, an identity of not less than 90%, an identity of not less than 95%, an identity of not less than 96%, an identity of not less than 97%, an identity of not less than 98% or an identity of not less than 99%.

If the identity is less than 80% when the P1 fluorescently labeled oligonucleotide of the present invention is compared with the sequence that has a sequence complementary to SEQ ID NO:1 and is complementary to SEQ ID NO:1 with the exception that its base corresponding to the 311th base is a guanine, then the detecticin sensitivity with respect to a sample nucleic acid including a mutant type of the ABCG2 gene will be lower.

The P1' fluorescently labeled oligonucleotide in the present invention needs to be able to hybridize under stringent conditions to a complementary strand of a base sequence having the same bases as SEQ ID NO:1 with the exception that the base corresponding to the 311st base in SEQ ID NO:1 is a guanine.

The hybridization may be carried out according to a known method or a method corresponding thereto, such as a method as described in Molecular Cloning 3rd (J. Sambrook et al., Cold Spring Harbor Lab. Press, 2001). This document is incorporated herein by reference.

The term "stringent conditions" means conditions in which specific hybrids are formed, but non-specific hybrids are not formed. Typical examples of the stringent conditions include, for example, conditions in which the hybridization is carried out at a potassium concentration from about 25 mM to about 50 mM and a magnesium concentration from about 1.0 mM to about 5.0 mM. One example of the conditions of the present invention is conditions in which the hybridization is carried out in Tris-HCl (pH 8.6), 25 mM KCl, and 1.5 mM $MgCl_2$, but examples of the conditions of the present invention are not limited thereto. Other examples of the stringent conditions are described in Molecular Cloning 3rd (J. Sambrook et al., Cold Spring Harbor Lab. Press, 2001). This document is incorporated herein by reference. Those skilled in the art may readily choose such conditions by changing the hybridization reaction and/or the salt concentration of the hybridization reaction solution.

Examples of a base sequence of the P1 or P1' fluorescently labeled oligonucleotide in the present invention are shown in Table 1 below, but the present invention is not limited to these.

In Table 1, the base corresponding to the 301st base of SEQ ID NO:1 is shown with a capital letter; and this table shows not only oligonucleotides in cases where their bases corresponding to the 301st base of SEQ ID NO:1 are a C, a T, an A or a G, but also the Tm values of the hybrids which are each formed by these fluorescently labeled oligonucleotides.

The Tm values were calculated by using MeltCalc© 99 FREE (meltcalc.com/) and under the set conditions of: Oligoconc. [µM] of 0.2 and Na eq. [mM] of 50.

NO:2 is a C (cytosine); but, in a mutant type thereof, the C has been mutated into a T (thymine).

In addition, in the wild type of the ABCG2 gene, the 126th amino acid in the amino acid sequence of the ABCG2 transporter is a glutamine (Gln); but, in a mutant type of the ABCG2 gene, the position is a termination codon (X) (this mutation is hereinafter referred to as "the Q126X mutation").

In the P2 or P2' fluorescently labeled oligonucleotide, a "base corresponding to the 251st base" is a C (cytosine) that is a base complementary to a G (guanine) of the 251st base of the base sequence indicated in SEQ ID NO:2.

In the P2 or P2' fluorescently labeled oligonucleotide, this complementary base C, which has been fluorescently labeled, may exist at a position of any one of 1st to 3rd positions from the 5' end of the oligonucleotide. Alternatively, the base may exist at the 5' end of the oligonucleotide. Thereby, for example, the sensitivity for detecting polymorphism may be further improved. In addition, the P2 fluorescently labeled oligonucleotide may be obtained with a good productivity.

The P2 or P2' fluorescently labeled oligonucleotide is a probe that is capable of detecting polymorphism of the 234th base of the base sequence indicated in SEQ ID NO:2. This base is a C in a wild type and a T in a mutant type.

The P2 or P2' fluorescently labeled oligonucleotide needs to have a length of from 18 bases to 50 bases. When the base length of the P2 or P2' fluorescently labeled oligonucleotide is a length of 17 bases or less or a length of 51 bases or more, the sensitivity for detecting polymorphism may be decreased. From the view point of the sensitivity for detecting polymor-

TABLE 1

| | mer | Tm(mt(A)) | Tm(WT(G)) | ⊿ | SEQ ID NO |
|---|---|---|---|---|---|
| agccattggtgtttccttgtgacaCtgggataaaaacttcgacattactg | 50 | 65.9 | 68.1 | 2.2 | 4 |
| cattggtgtttccttgtgacaCtgggataaaaacttcgac | 40 | 61.8 | 64.8 | 3 | 5 |
| ggtgtttccttgtgacaCtgggataaaaactt | 32 | 56.7 | 60.9 | 4.2 | 6 |
| ccttgtgacaTtggga | 16 | 46.5 | 39.6 | 6.9 | 7 |
| ccttgtgacaAtggga | 16 | 38 | 41.6 | 3.6 | 8 |
| cttgtgacaGtggg | 14 | 22.1 | 24.5 | 2.4 | 9 |

* ⊿ is the difference between Tm(mt(A)) and Tm(WT(G))

In the present invention, the difference between a Tm value in a case where the P1 or P1' fluorescently labeled oligonucleotide is hybridized with an oligonucleotide having a base sequence that is complementary to the base sequence of the P1 or P1' fluorescently labeled oligonucleotide (the Tm (mt (A)) in Table 1) and a Tm value in a case where the P1 or P1' fluorescently labeled oligonucleotide is hybridized with a DNA having a base sequence that is complementary to the base sequence of the P1 fluorescently labeled oligonucleotide with the exception that its base corresponding to the 301st base of SEQ ID NO:1 is non-complementary (the Tm (WT (G)) in Table 1) may be, for example, 1.0° C. or more, 2.0° C. or more, or 3.0° C. or more. When the difference between the Tm values is 4.0° C. or more, for example, a mutation of the 301st base of SEQ ID NO:1 may be detected with a higher sensitivity.

The base sequence indicated in SEQ ID NO:2 is a part of the base sequence of the ABCG2 gene, and corresponds to 480 bases which are the 26821st to the 27300th bases in the 1st to the 68595th bases of the ABCG2 gene.

In the wild type of the ABCG2 gene, a base corresponding to the 234th base of the base sequence indicated in SEQ ID phism, the base length of the P2 or P2' fluorescently labeled oligonucleotide may be a length of from 18 bases to 40 bases, a length of from 20 bases to 30 bases, or a length of from 22 bases to 26 bases.

By varying the base length of the P2 or P2' fluorescently labeled oligonucleotide, for example, the Tm value, which is a dissociation temperature of a hybrid formed by the P2 fluorescently labeled oligonucleotide and its target sequence, may be adjusted to a desired value.

The P2 fluorescently labeled oligonucleotide of the present invention has a homology with respect to a sequence that is complementary to the base sequence indicated in SEQ ID NO:2 with the exception that its base corresponding to the 251st base is a guanine.

More specifically, the P2 fluorescently labeled oligonucleotide of the present invention has an identity of not less than 80% with respect to a base sequence complementary to the base sequence indicated in SEQ ID NO:2.

In addition, from the view point of the detection sensitivity, the P2 fluorescently labeled oligonucleotide may have an identity of not less than 85%, an identity of not less than 90%, an identity of not less than 95%, an identity of not less than 96%, an identity of not less than 97%, an identity of not less than 98% or an identity of not less than 99%.

If the identity is less than 80% when the P2 fluorescently labeled oligonucleotide of the present invention is compared with the sequence that has a sequence complementary to SEQ ID NO:2 and is complementary to SEQ ID NO:2 with the exception that its base corresponding to the 251st base is a guanine, then the detection sensitivity with respect to a sample nucleic acid including a mutant type of the ABCG2 gene will be lower.

The P2' fluorescently labeled oligonucleotide in the present invention needs to be able to hybridize under stringent conditions to a complementary strand of a base sequence having the same bases as SEQ ID NO:2 with the exception that the base corresponding to the 251st base in SEQ ID NO:2 is a guanine. The hybridization may be carried out according to a method as described above, and, as the stringent conditions, conditions similar to the above-described conditions may be applied.

Examples of a base sequence of the P2 or P2' fluorescently labeled oligonucleotide in the present invention are shown in Table 2 below, but the present invention is not limited to these.

In Table 2, the base corresponding to the 234th base of SEQ ID NO:2 is shown with an underlined capital letter; and this table shows not only oligonucleotides in cases where their bases corresponding to the 234th base of SEQ ID NO:2 is an A, a G, a T or a C, but also the Tm values of the hybrids which are each formed by these fluorescently labeled oligonucleotides. The Tm values were calculated in the same manner as described above. The base shown with a capital letter that is not underlined is a base corresponding to the W at the 245th position of SEQ ID NO:2.

The base sequence indicated in SEQ ID NO:3 is a part of the base sequence of the ABCG2 gene, and corresponds to 341 bases which are the 27528th to the 27868th bases in the 1st to the 68595th bases of the ABCG2 gene.

In the wild type of the ABCG2 gene, a base corresponding to the 161st base of the base sequence indicated in SEQ ID NO:3 is a C (cytosine); but, in a mutant type thereof, the C has been mutated into an A (adenine).

In addition, in the wild type of the ABCG2 gene, the 141st amino acid in the amino acid sequence of the ABCG2 transporter is a glutamine (Gln); but, in a mutant type of the ABCG2 gene, the amino acid is a lysine (Lys) (this mutation is hereinafter referred to as "the Q141K mutation").

In the P3 or P3' fluorescently labeled oligonucleotide, a "base corresponding to the 152nd base" is a C (cytosine) that is a base complementary to a G (guanine) of the 152nd base of the base sequence indicated in SEQ ID NO:3.

In the P3 or P3' fluorescently labeled oligonucleotide, this complementary base C, which has been fluorescently labeled, may exist at a position of any one of 1st to 3rd positions from the 3' end of the oligonucleotide. Alternatively, the base may exist at the 3' end of the oligonucleotide. Thereby, for example, the sensitivity for detecting polymorphism may be further improved. In addition, the P3 or P3' fluorescently labeled oligonucleotide may be obtained with a good productivity.

The P3 or P3' fluorescently labeled oligonucleotide is a probe that is capable of detecting polymorphism of the 161st base of the base sequence indicated in SEQ ID NO:3. This base is a C in a wild type and an A in a mutant type.

The P3 or P3' fluorescently labeled oligonucleotide needs to have a length of from 10 bases to 50 bases. The base length

TABLE 2

| | mer | Tm(mt(T)) | Tm(WT(C)) | Δ | SEQ ID NO |
|---|---|---|---|---|---|
| gaaacagaggaaacagaaaatgcaaacccactAataattacttAtaccac | 50 | 64.2 | 63.2 | 1 | 10 |
| aacccactAatacttacttAtaccacgtaacctgaattac | 40 | 60.4 | 58.4 | 2 | 11 |
| cccactAatacttacttAtaccacgtaacctgaattac | 38 | 59.5 | 57.4 | 2.1 | 12 |
| aacccactAatacttacttAtaccacgtaacctg | 34 | 59.1 | 52.9 | 6.2 | 13 |
| cccactTatacttacttAtaccac | 24 | 49.8 | 45 | 4.8 | 14 |
| cccactTatacttacttGtaccac | 24 | 52.3 | 46.8 | 5.5 | 15 |
| tactt Ttaccac | 12 | 12 | 10.2 | 1.8 | 16 |
| TatacttacttCtaccac | 18 | 29.3 | 27.1 | 2.2 | 17 |

* Δ is the difference between Tm(mt(T)) and Tm(WT(C))

In the present invention, the difference between a Tm value in a case where the P2 or P2' fluorescently labeled oligonucleotide is hybridized with a DNA having a base sequence that is complementary to the base sequence of the P2 or P2' fluorescently labeled oligonucleotide (the Tm (mt (T)) in Table 1) and a Tm value in a case where the P2 or P2' fluorescently labeled oligonucleotide is hybridized with an oligonucleotide having a base sequence that is complementary to the base sequence of the P2 or P2' fluorescently labeled oligonucleotide with the exception that its base corresponding to the 234th base of SEQ ID NO:2 is non-complementary (the Tm (WT (C)) in Table 2) may be 1.0° C. or more, 2.0° C. or more, or 3.0° C. or more. When the difference between the Tm values is 4.0° C. or more, for example, a mutation of the 234th base of SEQ ID NO:2 may be detected with a higher sensitivity.

of the P3 or P3' fluorescently labeled oligonucleotide may be a length of from 10 bases to 40 bases, a length of from 15 bases to 30 bases, or a length of from 18 bases to 22 bases. When the base length is within any one of these ranges, for example, the sensitivity for detecting polymorphism may be further improved.

By varying the base length of the P3 or P3' fluorescently labeled oligonucleotide, for example, the Tm value, which is a dissociation temperature of a hybrid formed by the P3 fluorescently labeled oligonucleotide and its target sequence, may be adjusted to a desired value.

The P3 fluorescently labeled oligonucleotide of the present invention has a homology with respect to a sequence that is complementary to the base sequence indicated in SEQ ID NO:3 with the exception that its base corresponding to the 152nd base is a guanine.

More specifically, the P3 fluorescently labeled oligonucleotide of the present invention has an identity of not less than 80% with respect to a base sequence complementary to the base sequence indicated in SEQ ID NO:3.

In addition, from the view point of the detection sensitivity, the P3 fluorescently labeled oligonucleotide may have an identity of not less than 85%, an identity of not less than 90%, an identity of not less than 95%, an identity of not less than 96%, an identity of not less than 97%, an identity of not less than 98% or an identity of not less than 99%.

If the identity is less than 80% when the P3 fluorescently labeled oligonucleotide of the present invention is compared with the sequence that has a sequence complementary to SEQ ID NO:3 and is complementary to SEQ ID NO:3 with the exception that its base corresponding to the 152nd base is a guanine, then the detection sensitivity with respect to a sample nucleic acid including a mutant type of the ABCG2 gene will be lower.

The P3' fluorescently labeled oligonucleotide in the present invention needs to be able to hybridize under stringent conditions to a complementary strand of a base sequence having the same bases as SEQ ID NO:3 with the exception that the base corresponding to the 152nd base in SEQ ID NO:3 is a guanine. The hybridization may be carried out according to a method as described above, and, as the stringent conditions, conditions similar to the above-described conditions may be applied.

Examples of a base sequence of the P3 or P3' fluorescently labeled oligonucleotide in the present invention are shown in Table 3 below, but the present invention is not limited to these.

In Table 3, the base corresponding to the 161st base of SEQ ID NO:3 is shown with a capital letter; and this table shows not only oligonucleotides in cases where their bases corresponding to the 161st base of SEQ ID NO:3 is a T, a G, an A or a C, but also the Tm values of the hybrids which are each formed by these fluorescently labeled oligonucleotides. The Tm values were calculated in the same manner as described above.

between the Tm values is 4.0° C. or more, for example, a mutation of the 161st base of SEQ ID NO:3 may be detected with a higher sensitivity.

As the P1, the P1', the P2, the P2', the P3 or the P3' fluorescently labeled oligonucleotide in the present invention, a fluorescently labeled oligonucleotide having a sequence wherein a base(s) has been inserted into, deleted from and/or substituted in any one of the P1, the P1', the P2, the P2', the P3 or the P3' fluorescently labeled oligonucleotide is also encompassed.

The fluorescently labeled oligonucleotide having a sequence wherein a base(s) has been inserted, deleted and/or substituted is not particularly limited, as long as the oligonucleotide exhibits an effect similar to that of any one of the P1, the P1', the P2, the P2', the P3 or the P3' fluorescently labeled oligonucleotide; and, in cases where a base(s) has been inserted, deleted and/or substituted, the position(s) of the insertion(s), deletion(s) and/or substitution(s) is not particularly limited. The number of bases that have been inserted, deleted and/or substituted may be, for example, 1 base, or 2 or more bases, such as from 1 base to 10 bases, or from 1 base to 5 bases.

The fluorescently labeled oligonucleotide of the present invention may be a fluorescently labeled oligonucleotide in which the fluorescence intensity at the time when the oligonucleotide is hybridized to its target sequence is decreased (quenched) or increased as compared to the fluorescence intensity at the time when the oligonucleotide is not hybridized to its target sequence. In particular, the fluorescently labeled oligonucleotide of the present invention may be a fluorescently labeled oligonucleotide in which the fluorescence intensity at the time when the oligonucleotide is hybridized to its target sequence is decreased as compared to the fluorescence intensity at the time when the oligonucleotide is not hybridized to its target sequence.

A probe that uses the "fluorescence quenching phenomenon" as described above is generally referred to as a guanine quenching probe, and it is known as Q PROBE®. Among

TABLE 3

| | mer | Tm(mt(A)) | Tm(WT (C)) | Δ | SEQ ID NO |
|---|---|---|---|---|---|
| ttgcaagccgaagagctgctgagaactGtaagttttctctcaccgtcagag | 51 | 69.3 | 71.1 | 1.8 | 18 |
| gccgaagagctgctgagaactGtaagttttctctcaccgt | 40 | 65.9 | 68.3 | 2.4 | 19 |
| gagctgctgagaactGtaagttttctctca | 30 | 56.1 | 60.1 | 4 | 20 |
| gctgagaactTtaagttttc | 20 | 46.6 | 39.6 | 7 | 21 |
| ctAtaagttttc | 12 | 5.1 | 2.6 | 2.5 | 22 |
| ctCtaagttttc | 12 | 0 | 1.2 | 1.2 | 23 |

*Δ is the difference between Tm(mt(A)) and Tm(WT(C))

In the present invention, the difference between a Tm value in case where the P3 or P3' fluorescently labeled oligonucleotide is hybridized with an oligonucleotide having a base sequence that is complementary to the base sequence of the P3 or P3' fluorescently labeled oligonucleotide (the Tm (mt (A)) in Table 1) and a Tm value in case where the P3 or P3' fluorescently labeled oligonucleotide is hybridized with a DNA having a base sequence that is complementary to the base sequence of the P3 or P3' fluorescently labeled oligonucleotide with the exception that its base corresponding to the 161st base of SEQ ID NO:3 is non-complementary (the Tm (WT (C)) in Table 3) may be, for example, 1.0° C. or more, 2.0° C. or more, or 3.0° C. or more. When the difference such probes, an oligonucleotide which has been designed so that its 3' or 5' end is a cytosine (C) and which has been labeled with a fluorescent dye so that the fluorescence emission is reduced when the C at the 3' or 5' end comes close to a guanine (G) is especially preferable. By using such a probe, the hybridization and dissociation of the probe may be readily checked by the change in its signal.

A known detection method other than the detection method using a Q PROBE® may also be applied. Examples of such a detection method include a TAQ-MAN probe method, a hybridization probe method, a molecular beacon method, and a MGB probe method.

The fluorescent dye is not particularly limited, and examples of the fluorescent dye include fluorescein, phosphor, rhodamine and polymethine dye derivatives. Examples of commercially available products of such fluorescent dyes include Pacific Blue, BODIPY FL, FluorePrime, Fluoredite, FAM, Cy3 and Cy5, and TAMRA.

The detection conditions of the fluorescent-labeled oligonucleotide are not particularly limited, and may be decided, as appropriate, in accordance with the fluorescent dye to be used. For example, Pacific Blue can be detected at a detection wavelength of from 445 nm to 480 nm, TAMRA can be detected at a detection wavelength of from 585 nm to 700 nm, and BODIPY FL can be detected at a detection wavelength of from 520 nm to 555 nm.

By using a probe having such a fluorescent dye, hybridization and dissociation of the probe can be readily confirmed based on a change in fluorescence signal thereof. Attachment of a fluorescent dye to the oligonucleotide may be carried out according to an ordinary method, such as a method described in JP-A No. 2002-119291.

It should be noted that, in the present invention, the same fluorescent dye may be used, or alternatively, different fluorescent dyes may be used to label one or more of the oligonucleotide.

In addition, the fluorescent-labeled oligonucleotide may have, for example, a phosphate group added to its 3' end. Addition of a phosphate group to the 3' end of the fluorescent-labeled oligonucleotide sufficiently suppresses elongation of the probe itself by a gene amplification reaction. As described below, a DNA for which the presence or absence of a mutation should be detected (target DNA) may be prepared using a gene amplification method such as PCR. When the fluorescent-labeled oligonucleotide that has a phosphate group added to its 3' end is used, the amplification reaction can be carried out even in the presence of the oligonucleotide in a reaction solution of the amplification reaction. Since the fluorescently labeled oligonucleotide has a phosphate group at the 3' end, extension of the probe itself by the gene amplification reaction may be effectively inhibited.

A similar effect can be obtained also by adding a labeling substance (a fluorescent dye) as described above to the 3' end.

Specific examples of an oligonucleotide which has the above-described base sequence and whose C base at the 5' or 3' end is labeled with a fluorescent dye are shown below (the bases indicated with a capital letter each represent a mutation point; the P represents a phosphate group; and the "(Pacific Blue)," the "(FL)" and the "(TAMRA)" each represent a fluorescent dye as described above). However, the fluorescently labeled oligonucleotide in the present invention is not limited to those described below.

The P1, the P1', the P2, the P2', the P3 or the P3' fluorescently labeled oligonucleotides according to the present invention may be produced according to a conventional method known as a method for synthesizing an oligonucleotide, such as a method as described in JP-A No. 2002-119291.

<Polymorphism Detection Method>

The method of detecting polymorphism is not particularly limited, as long as it is a method in which polymorphism in the ABCG2 gene may be detected by using the fluorescently labeled nucleotide as described above. As an example of the method of detecting polymorphism in which the fluorescently labeled nucleotide as described above is used, a method of detecting polymorphism using Tm analysis is described below.

The method of detecting polymorphism of the present invention is a method of detecting polymorphism in the ABCG2 gene, and is characterized by including the below-described processes (I) to (IV). In addition, the characteristic of the method of detecting polymorphism of the present invention resides in that the polymorphism detection probe including the above-described fluorescently labeled nucleotide is used; and therefore the configuration, conditions and/or the like of the method are not particularly limited by the explanation described below.

Process (I): contacting the fluorescent-labeled probe with a single-stranded nucleic acid in a sample, to obtain a hybrid.

Process (II): dissociating the hybrid by changing the temperature of the sample containing the hybrid, and measuring a change in fluorescence signal due to the dissociation of the hybrid.

Process (III): measuring a Tm value, which is the dissociation temperature of the hybrid, based on the change in fluorescence signal.

Process (IV): detecting the presence of the ABCG2 gene mutation on the single-stranded nucleic acid in the sample, based on the Tm value.

Further, in addition to the aforementioned processes (I) to (IV), the detection method according to the present invention may include the following process (V).

Process (V): determining the abundance ratio of single-stranded nucleic acid having the gene mutation in the total single-stranded nucleic acids contained in the sample, based on the presence of the gene mutation.

The measurement of the Tm value in the process (III) may include not only measuring the dissociation temperature of the hybrid, but also measuring the differential values of the fluorescence signal that changes according to the temperature when the hybrid is melted.

TABLE 4

| Name | Sequence | (mer) |
|---|---|---|
| 5PB-ABCG2 V12M-A-R1 | (Pacific Blue)-ccttgtgacaTtggga-(P) | 16 |
| 5FL-ABCG2 Q126X-T-R1 | (FL)-cccactTatacttacttAtaccac-(P) | 24 |
| 3T-ABCG2-mt-R1 | gctgagaactTtaagttttc-(TAMRA) | 20 |

The fluorescently labeled oligonucleotide may be used as a polymorphism detection probe for detecting polymorphism in the ABCG2 gene, and particularly the V12M mutation, the Q126X mutation or the Q141K mutation.

In addition, the probe for detecting polymorphism in the ABCG2 gene may be used as a probe for melting curve analysis.

In the present invention, the nucleic acid in the sample may be a single-stranded nucleic acid or a double-stranded nucleic acid. In a case in which the nucleic acid is a double-stranded nucleic acid, the method may include, for example, melting (dissociating) the double-stranded nucleic acid in the sample into single-stranded nucleic acids by heating before being hybridized with the fluorescent-labeled probe. The dissociation of a double-stranded nucleic acid into single-stranded nucleic acids enables hybridization with the fluorescent-labeled probe.

In the present invention, the nucleic acid contained in the sample to be detected may be, for example, a nucleic acid originally contained in a biological sample, or an amplification product obtained by amplifying a region of the gene of interest that contains a mutated site(s) of the ABCG2 gene by PCR or the like using a nucleic acid originally contained in a biological sample as a template with a view to improving the detection accuracy. The length of the amplification product is not particularly limited, and may be, for example, a length of from 50 mer to 1000 mer, or a length of from 80 mer to 200 mer. Furthermore, the nucleic acid in the sample may be, for example, a cDNA that has been synthesized from RNAs derived from a biological sample (e.g., total RNAs, mRNAs, etc.) by RT-PCR (Reverse Transcription PCR).

In the present invention, the addition ratio (molar ratio) of the probe according to the present invention relative to the nucleic acids in the sample is not particularly limited. The amount of the probe to be added may be, for example, no more than 1 times (by mol) the amount of DNAs in the sample. From the viewpoint of ensuring a sufficient detection signal, the addition ratio of the probe according to the present invention to be added relative to the nucleic acids in the sample (in a molar ratio) may be 0.1 or lower.

The "nucleic acids in the sample" may be, for example, a total of nucleic acids to be detected that have the gene mutation to be detected and nucleic acids, other than the nucleic acids to be detected, that do not have the gene mutation, or a total of amplification products containing a detection target sequence having the gene mutation to be detected and amplification products containing a sequence, other than the detection target sequence, that does not have the gene mutation. Although the ratio of the nucleic acid to be detected relative to nucleic acids in the sample is usually unknown in advance, the consequential addition ratio of the probe relative to the nucleic acids to be detected (or the amplification products containing a sequence to be detected) (in a molar ratio) may be 10 or lower. The addition ratio of the probe relative to the nucleic acids to be detected (or the amplification products containing a sequence to be detected) (in a molar ratio) may be 5 or lower, or 3 or lower. The lower limit of the ratio is not particularly limited, and may be, for example, 0.001 or higher, 0.01 or higher, or 0.1 or higher.

The above-described addition ratio of the fluorescent-labeled probe according to the present invention relative to DNAs may be, for example, a molar ratio relative to double-stranded nucleic acids or a molar ratio relative to single-stranded nucleic acids.

In the present invention, the measurement of a change in the signal caused by a temperature change for determining a Tm value may be carried out by measuring the absorbance at 260 nm on the basis of the principle described above. However, the measurement may be carried out by measuring a signal which is based on a signal from the label attached to the fluorescent-labeled probe, and which varies in accordance with the degree of the formation of a hybrid of a single-stranded DNA and the probe. Therefore, the above-described fluorescent-labeled oligonucleotide may be used as the fluorescent-labeled probe. Examples of the fluorescent-labeled P1, P1', P2, P2', P3 or P3' oligonucleotide (hereinafter sometimes collectively referred to as "fluorescent-labeled oligonucleotide") include a fluorescent-labeled oligonucleotide of which the fluorescence intensity when the oligonucleotide is hybridized with a target sequence thereof is decreased (quenched) as compared to the fluorescence intensity when the oligonucleotide is not hybridized with the target sequence thereof, and a fluorescent-labeled oligonucleotide of which the fluorescence intensity when the oligonucleotide is hybridized with a target sequence thereof is increased as compared to the fluorescence intensity when the oligonucleotide is not hybridized with the target sequence thereof.

The former fluorescent-labeled oligonucleotide does not show a fluorescence signal or only a weak fluorescence signal when the fluorescent-labeled oligonucleotide forms a hybrid (a double-stranded DNA) with the sequence to be detected; however, the fluorescent-labeled oligonucleotide becomes to show a fluorescence signal or shows an increased fluorescence signal when the fluorescent-labeled oligonucleotide is dissociated by heating.

The latter fluorescent-labeled oligonucleotide shows a fluorescence signal when the fluorescent-labeled oligonucleotide forms a hybrid (a double-stranded DNA) with the sequence to be detected; however, the fluorescent-labeled oligonucleotide shows a decreased fluorescence signal or ceases to show a fluorescent signal when the fluorescent-labeled oligonucleotide is dissociated by heating. Therefore, similar to the measurement of the absorbance at 260 nm described above, the progress of melting can be monitored, and the Tm value can be determined by detecting the change in the fluorescence signal from the fluorescent label under the conditions specific to the fluorescent label (for example, the fluorescence wavelength thereof).

The method for detecting the change in the signal based on a signal from the fluorescent dye in the polymorphism detection method according to the present invention is described below by way of specific examples. The polymorphism detection method according to the present invention has a feature of using the fluorescent-labeled polymorphism detection probe, and other processes and conditions of the method are not limited in any way.

The sample containing a nucleic acid that serves as a template for nucleic acid amplification is not particularly limited as long as the sample contains a nucleic acid, particularly the ABCG2 gene. Examples of such a sample include a sample that is derived from or can be derived from any biological source, examples of which include: a tissue such as colon or lung; a hemocyte such as a leukocyte cell; whole blood; plasma; a sputum; a suspension of oral mucosa; a somatic cell of nail, hair or the like; a germ cell; milk; ascitic fluid; a paraffin-embedded tissue; gastric juice; a gastric lavage fluid; urine; peritoneal fluid; amniotic fluid; and a cell culture. The method for sampling the sample, the method for preparing the sample containing a nucleic acid, and the like are not limited, and, conventional methods known in the art may be employed therefor. A nucleic acid obtained from such a biological source may be directly used as the template, or may be used after the sample has been subjected to pretreatment that modifies the properties of the sample.

For example, in a case in which whole blood is used as the sample, the isolation of genomic DNA from the whole blood may be carried out by a conventional method known in the art. For example, a commercially available genomic DNA isolation kit (trade name: GFX GENOMIC BLOOD DNA PURIFICATION KIT, available from GE Healthcare Biosciences), etc. may be used.

Examples of a base sequence of a single-stranded nucleic acid that may be used in the method of detecting polymorphism of the present invention are shown below. These are exemplary, and therefore, the present invention is not limited to these.

As a single-stranded nucleic acid for detecting the polymorphism of the 301st base of the base sequence indicated in SEQ ID NO:1, at least one single-stranded nucleic acid selected from the group consisting of the base sequences described below may be used.

TABLE 5

| Name | Sequence | (mer) | SEQ ID NO |
|---|---|---|---|
| ABCG2-V12M-50-F-WT | cagtaatgtcgaagttttatcccaGtgtcacaaggaaacaccaatggct | 50 | 24 |
| ABCG2-V12M-50-F-mt | cagtaatgtcgaagttttatcccaAtgtcacaaggaaacaccaatggct | 50 | 25 |
| ABCG2-V12M-50-R-WT | agccattggtgtttccttgtgacaCtgggataaaaacttcgacattactg | 50 | 26 |
| ABCG2-V12M-50-R-mt | agccattggtgtttccttgtgacaTtgggataaaaacttcgacattactg | 50 | 27 |

As a single-stranded nucleic acid for detecting the polymorphism of the 234th base of the base sequence indicated in SEQ ID NO:2, at least one single-stranded nucleic acid selected from the group consisting of the base sequences described below may be used.

TABLE 6

| Name | Sequence | (mer) | SEQ ID NO |
|---|---|---|---|
| ABCG2-Q126X-50-F-WT | caaatgtaattcaggttacgtggtaCaagtaagtatTagtgggtttgcat | 50 | 28 |
| ABCG2-Q126X-50-F-mt | caaatgtaattcaggttacgtggtaTaagtaagtatTagtgggtttgcat | 50 | 29 |
| ABCG2-Q126X-40-F-WTC | ggttaCgtggtaCaagtaagtatCagtgggtttgcatttt | 40 | 30 |
| ABCG2-Q126X-40-F-mtC | ggttaCgtggtaTaagtaagtatCagtgggtttgcatttt | 40 | 31 |

As a single-stranded nucleic acid for detecting the polymorphism of the 161st base of the base sequence indicated in SEQ ID NO:3, at least one single-stranded nucleic acid selected from the group consisting of the base sequences described below may be used.

TABLE 7

| Name | Sequence | (mer) | SEQ ID NO |
|---|---|---|---|
| ABCG2-mt-F-40 | acggtgagagaaaacttaAagttctcagcagctcttcggc | 40 | 32 |
| ABCG2-WT-F-40 | acggtgagagaaaacttaCagttctcagcagctcttcggc | 40 | 33 |

Next, a fluorescent-labeled polymorphism detection probe including the fluorescent-labeled oligonucleotide is added to the sample containing an isolated genomic DNA.

The fluorescent-labeled probe may be added to a liquid sample containing an isolated genomic DNA, or may be mixed with a genomic DNA in an appropriate solvent. The solvent is not particularly limited, and examples of the solvent include conventional solvents known in the art, such as: a buffer solution such as Tris-HCl; a solvent containing at least one of KCl, $MgCl_2$, $MgSO_4$, or glycerol; and a PCR reaction solution.

The timing of adding the fluorescent-labeled probe is not particularly limited. For example, in a case in which an amplification process such as PCR described below is carried out, the fluorescent-labeled probe may be added to the PCR amplification products after the amplification process is carried out, or may be added before the amplification process is carried out.

In a case in which the fluorescent-labeled probe is added before an amplification process such as PCR is carried out, for example, a fluorescent dye or a phosphate group may have been added to the 3' end of the probe, as described above.

The method of amplifying a nucleic acid may be, for example, a method in which a polymerase is employed. Examples of thereof include a PCR method, an ICAN method, a LAMP method, and an NASBA method. In a case in which the amplification is carried out by a method in which a polymerase is employed, the amplification may be carried out in the presence of the fluorescent-labeled probe according to the present invention. Those skilled in the art would be able to easily adjust the reaction conditions of the amplification and the like in accordance with the fluorescent-labeled probe and the polymerase to be used. In a case in which the amplification is carried out in the presence of the fluorescent-labeled probe according to the present invention, a gene mutation can be detected by only analyzing the Tm value of the fluorescent-labeled probe after the amplification of the nucleic acid is carried out, and, therefore, it is not necessary to separate the amplification product after completion of the reaction. Thus, contamination by the amplification product does not occur. In addition, since the detection can be carried out by the same apparatus as the apparatus required for the amplification, conveyance of a vessel is unnecessary, and automatization of the process is facilitated.

The DNA polymerase to be used in the PCR method may be selected, without particular limitation, from DNA polymerases that are usually used for PCR. Examples of the DNA polymerase include GENE TAQ (trade name, manufactured by NIPPON GENE CO., LTD.), PRIMESTAR MAX DNA POLYMERASE (trade name, manufactured by Takara Bio Inc.), and a Taq polymerase.

The amount of the polymerase to be used is not particularly limited as long as a usually-applied polymerase concentration is provided. For example, in a case in which a Taq polymerase is used, the concentration of the Taq polymerase may be, for example, a concentration of from 0.01 U to 100 U relative to 50 μl of the reaction solution. In this range, for example, the sensitivity of the detection of polymorphism in the ABCG2 gene tends to be increased.

The PCR method may be carried out under the conditions appropriately selected from usually-employed conditions.

When the amplification is carried out, the amplification may be monitored using real-time PCR so that the copy number of the DNA (a sequence to be detected) contained in the sample can be measured. In other words, the proportion of probes forming hybrids is increased as the amplification of the DNA (a sequence to be detected) by PCR proceeds, thereby changing the fluorescence intensity. By monitoring the change in the fluorescence intensity, the copy number and/or the abundance ratio of the sequence to be detected (either a normal DNA or a mutant DNA) contained in the sample can be obtained.

In the polymorphism detection method according to the present invention, the fluorescent-labeled oligonucleotide and a single-stranded nucleic acid in the sample are brought into contact with each other, thereby allowing hybridization thereof. The single-stranded nucleic acid in the sample can be prepared by, for example, dissociating the PCR amplification products obtained in the above-described manner.

The heating temperature employed for dissociation of the PCR amplification products (the heating temperature in the dissociation process) is not particularly limited as long as it is a temperature at which the amplification products can be dissociated. For example, the heating temperature may be in the range of from 85° C. to 95° C. The heating time is not particularly limited, either. The heating time may be, for example, in the range of from 1 second to 10 minutes, or from 1 second to 5 minutes.

The hybridization of the dissociated single-stranded DNA and the fluorescent-labeled oligonucleotide may be carried out by, for example, decreasing, after the dissociation process, the temperature from the heating temperature employed in the dissociation process. The temperature condition for the hybridization may be, for example, in the range of from 40° C. to 50° C.

The volume and concentration of each component in the reaction solution in the hybridization process are not particularly limited. In regard to specific examples thereof, the concentration of DNAs in the reaction solution may be, for example, a concentration of from 0.01 μM to 1 μM, or a concentration of from 0.1 μM to 0.5 μM. The concentration of the fluorescent-labeled oligonucleotide may be, for example, in a range in which the above-described addition ratio relative to DNAs is satisfied, and may be, for example, a concentration of from 0.001 μM to 10 μM, or a concentration of from 0.001 μM to 1 μM.

The resultant hybrid of the single-stranded DNA and the fluorescent-labeled oligonucleotide is gradually heated, and a change in fluorescence signal caused by the temperature increase is measured. For example, in the case of using Q PROBE®, the fluorescence intensity in the state of being hybridized with the single-stranded DNA is decreased (or quenched) as compared to the fluorescence intensity in the dissociated state. Therefore, for example, the hybrid emitting decreased fluorescence or the quenched hybrid may be gradually heated, and an increase in fluorescence intensity caused by the temperature increase may be measured.

The temperature range in which the change in fluorescence intensity is measured is not particularly limited, and the initial temperature may be, for example, a temperature of from room temperature to 85° C., or a temperature of from 25° C. to 70° C. The final temperature may be, for example, a temperature of from 40° C. to 105° C. The temperature increase rate is not particularly limited, either, and may be, for example, in the range of from 0.1° C./sec to 20° C./sec, or in the range of from 0.3° C./sec to 5° C./sec.

Next, the change in the signal is analyzed to determine the Tm value. More specifically, the Tm value may be determined by calculating a differential value at each temperature (−d(Fluorescence Intensity)/dt) from the fluorescent intensity obtained, and taking the temperature at which the differential value takes the lowest value as the Tm value. The Tm value may alternatively be determined as the point at which the increase in fluorescence intensity per unit time ((Increase in Fluorescence Intensity)/t) takes the largest value. On the contrary, in a case in which a probe of which signal intensity is increased by the formation of the hybrid, rather than a quenching probe, is used as the fluorescent-labeled probe, the signal analysis and the determination of the Tm value may be carried out by measuring a decrease in fluorescence intensity.

In the present invention, a change in fluorescence signal caused by a temperature increase (preferably an increase in fluorescence intensity) may be measured while heating the hybrid as described above. However, instead of this method, the measurement of a change in signal may alternatively be carried out, for example, in the course of hybrid formation. In other words, the temperature of the sample, to which the probe has been added, may be decreased, and a change in fluorescence signal caused by the temperature decrease may be measured in the course of hybrid formation.

For example, in case in which Q PROBE® is used, the fluorescence intensity is high when the probe is added to the sample since the probe is in the dissociated state. However, when the hybrid is formed by temperature decrease, the fluorescence is decreased (or quenched). Therefore, for example, a decrease in fluorescence intensity caused by temperature decrease may be measured while gradually decreasing the temperature of the heated sample.

On the other hand, in a case in which a probe of which signal is increased by hybrid formation is used, the fluorescence intensity is low (or quenched) when the probe is added to the sample since the probe is in the dissociated state. However, when the hybrid is formed by temperature decrease, the fluorescence intensity is increased. Therefore, for example, an increase in fluorescence intensity caused by temperature decrease may be measured while gradually decreasing the temperature of the sample.

In the method of detecting polymorphism of the present invention, as long as it is possible to amplify a region containing the intended base(s), a method of amplification is not particularly limited, and for example, the PCR method described above may be used.

Examples of the region containing the intended base(s) include a region having a length of from 50 bases to 500 bases in a base sequence containing the 301st base in the base sequence indicated in SEQ ID NO:1, a region having a length of from 50 bases to 300 bases in a base sequence containing the 234th base in the base sequence indicated in SEQ ID NO:2, and a region having a length of from 50 bases to 200 bases in a base sequence containing the 141st base in the base sequence indicated SEQ ID NO:3.

The primer to be applied to the PCR method is not particularly limited, as long as it is capable of amplifying a region to which the probe of the present invention may be hybridized. Such a primer may be properly designed based on the base sequence indicated un SEQ ID NO:1 by those skilled in the art. The length and Tm value of the primer may be a length of from 12 mer to 40 mer and a value of from 40° C. to 70° C., or a length of from 16 mer to 30 mer and a value of from 55° C. to 60° C.

The lengths of individual primers in a primer set do not need to be the same, although the Tm values of these primers are preferably approximately the same (or the difference between the Tm values of these primers is preferably within 5° C.).

Examples of the primers that may be used for amplifying a base sequence containing a region to which the probe of the present invention in the polymorphism detection method of the present invention may be hybridized are shown below. These are exemplary and therefore the present invention is not limited to these.

A primer for detecting polymorphism of the 301st base of the base sequence indicated in SEQ ID NO:1 may be at least one of a P4 oligonucleotide or a P5 oligonucleotide as described below.

The P4 oligonucleotide is an oligonucleotide having an identity of at least 80% with respect to a base sequence including the 198th to the 230th bases of the base sequence indicated in SEQ ID NO:1 and having a length of from 33 bases to 50 bases. The P4 oligonucleotide may be an oligonucleotide which may hybridize under stringent conditions to a complementary strand of a base sequence including bases corresponding to the 198th to the 230th bases of the base sequence indicated in SEQ ID NO:1 and having a length of from 33 bases to 50 bases. Furthermore, the P4 oligonucleotide may be an oligonucleotide having a sequence wherein a base(s) has been inserted into, deleted from and/or substituted in the P4 oligonucleotide.

The P5 oligonucleotide is an oligonucleotide having an identity of at least 80% with respect to a sequence that is complementary to a base sequence including the 332nd to the 353rd bases of the base sequence indicated in SEQ ID NO:1 and having a length of from 22 bases to 50 bases. The P5 oligonucleotide may be an oligonucleotide which may hybridize under stringent conditions to a complementary strand of a base sequence including bases corresponding to the 332nd to the 353rd bases of the base sequence indicated in SEQ ID NO:1 and having a length of from 22 bases to 50 bases. Furthermore, the P5 oligonucleotide may be an oligonucleotide having a sequence wherein a base(s) has been inserted into, deleted from and/or substituted in the P5 oligonucleotide.

Examples of a primer that may be used for amplifying a region containing the 301st base of the base sequence indicated in SEQ ID NO:1 in the method of detecting polymorphism of the present invention are shown below.

TABLE 8

| Name | Sequence | (mer) | SEQ ID NO |
|---|---|---|---|
| ABCG2-V12M-F2 | gcaatctcatttatctggactatcaacttacta | 33 | 34 |
| ABCG2-V12M-R1 | ttcaggtcattggaagctgtcg | 22 | 35 |

In order to detect the polymorphism of the 301st base of the base sequence indicated in SEQ ID NO:1, the P4 oligonucleotide and the P5 oligonucleotide may be used as a set of paired primers.

A primer for detecting polymorphism of the 234th base of the base sequence indicated in SEQ ID NO:2 may be at least one of a P6 oligonucleotide or a P7 oligonucleotide as described below.

The P6 oligonucleotide is an oligonucleotide having an identity of at least 80% with respect to a base sequence including the 132nd to the 157th bases of the base sequence indicated in SEQ ID NO:2 and having a length of from 26 bases to 50 bases. The P6 oligonucleotide may be an oligonucleotide which may hybridize under stringent conditions to a complementary strand of a base sequence including bases corresponding to the 132nd to the 157th bases of the base sequence indicated in SEQ ID NO:2 and having a length of from 26 bases to 50 bases. Furthermore, the P6 oligonucleotide may be an oligonucleotide having a sequence wherein a base(s) has been inserted into, deleted from and/or substituted in the P6 oligonucleotide.

The P7 oligonucleotide is an oligonucleotide having an identity of at least 80% with respect to a sequence that is complementary to a base sequence including the 268th to the 295th bases of the base sequence indicated in SEQ ID NO:2 and having a length of from 28 bases to 50 bases. The P7 oligonucleotide may be an oligonucleotide which may hybridize under stringent conditions to a complementary strand of a base sequence including bases corresponding to the 268th to the 295th bases of the base sequence indicated in SEQ ID NO:2 and having a length of from 28 bases to 50 bases. Furthermore, the P7 oligonucleotide may be an oligonucleotide having a sequence wherein a base(s) has been inserted into, deleted from and/or substituted in the P7 oligonucleotide.

Examples of a primer that may be used for amplifying a region containing the 234th base of the base sequence indicated in SEQ ID NO:2 in the method of detecting polymorphism of the present invention are shown below.

TABLE 9

| Name | Sequence | (mer) | SEQ ID NO |
|---|---|---|---|
| ABCG2-Q126X-F2 | gtcttagctgcaaggaaagatccaag | 26 | 36 |
| ABCG2-Q126X-R1 | aaagcacttacccatatagaaacagagg | 28 | 37 |

In order to detect the polymorphism of the 234th base of the base sequence indicated in SEQ ID NO:2, the P6 oligonucleotide and the P7 oligonucleotide may be used as a set of paired primers.

A primer for detecting polymorphism of the 161st base of the base sequence indicated in SEQ ID NO:3 may be at least one of a P8 oligonucleotide or a P9 oligonucleotide as described below.

The P8 oligonucleotide is an oligonucleotide having an identity of at least 80% with respect to a base sequence including the 121st to the 145th bases of the base sequence indicated in SEQ ID NO:3 and having a length of from 25 bases to 50 bases. The P8 oligonucleotide may be an oligonucleotide which may hybridize under stringent conditions to a complementary strand of a base sequence including bases corresponding to the 121st to the 145th bases of the base sequence indicated in SEQ ID NO:3 and having a length of from 25 bases to 50 bases. Furthermore, the P8 oligonucleotide may be an oligonucleotide having a sequence wherein a base(s) has been inserted into, deleted from and/or substituted in the P8 oligonucleotide.

The P9 oligonucleotide is an oligonucleotide having an identity of at least 80% with respect to a sequence that is complementary to a base sequence including the 214th to the 235th bases of the base sequence indicated in SEQ ID NO:3 and having a length of from 22 bases to 50 bases. The P9 oligonucleotide may be an oligonucleotide which may hybridize under stringent conditions to a complementary strand of a base sequence including bases corresponding to the 214th to the 235th bases of the base sequence indicated in SEQ ID NO:3 and having a length of from 22 bases to 50 bases. Furthermore, the P9 oligonucleotide may be an oligonucleotide having a sequence wherein a base(s) has been inserted into, deleted from and/or substituted in the P9 oligonucleotide.

Examples of a primer that may be used for amplifying a region containing the 161st base of the base sequence indicated in SEQ ID NO:3 in the method of detecting polymorphism of the present invention are shown below.

TABLE 10

| Name | Sequence | (mer) | SEQ ID NO |
|---|---|---|---|
| ABCG2-F1 | tgatgttgtgatgggcactctgacg | 25 | 38 |
| ABCG2-R2 | aatgaccctgttaatccgttcg | 22 | 39 |

In order to detect the polymorphism of the 161st base of the base sequence indicated in SEQ ID NO:3, the P8 oligonucleotide and the P9 oligonucleotide may be used as a set of paired primers.

The hybridization may be carried out according to a method as described in the section which describes the probe, and, as the stringent conditions, conditions similar to the conditions described in the section which describes the probe may be applied. The range of the identity, and an insertion, a deletion and a substitution to be applied may also be similar to those described in the section which describes the probe.

In the method of detecting polymorphism of the present invention, two or more of the P1, the P1', the P2, the P2' the P3 or the P3' fluorescently labeled oligonucleotides may be used in combination as the probe for detecting polymorphism of the present invention. This may make it possible to detect polymorphisms in the ABCG2 gene at the same time and easily.

In addition, by using two or more of the P1, the P1', the P2, the P2' the P3 or the P3' fluorescently labeled oligonucleotides in combination and detecting at least two mutations selected from the group consisting of the V12M mutation, the Q126X mutation and the Q141K mutation, for example, the function of an ABCG2 transporter derived from the ABCG2 gene may be predicted with a better accuracy. Examples of a combination of such oligonucleotides include, for example, a combination of the P1 fluorescently labeled oligonucleotide and the P2 fluorescently labeled oligonucleotide, or a combination of the P2 fluorescently labeled oligonucleotide and the P3 fluorescently labeled oligonucleotide, and especially a combination of the P2 fluorescently labeled oligonucleotide and the P3 fluorescently labeled oligonucleotide.

<Method of Evaluating Drug Efficacy or Tolerance>

The method of evaluating a drug efficacy or tolerance of the present invention includes detecting polymorphism in the ABCG2 gene by the above-described polymorphism detection method, and evaluating tolerance to the drug or the efficacy of the drug based on the results of the detection.

According to the method of detecting polymorphism in the ABCG2 gene of the present invention, the presence or absence of a mutation(s) in the ABCG2 gene and the type thereof, particularly the V12M mutation, the Q126X mutation and/or the Q141K mutation, may be detected with a high sensitivity and easily.

Thereby, evaluating of the tolerance to the drug and/or the efficacy of the drug may be carried out based on the detected presence or absence of polymorphism(s) and/or the abundance ratio of a mutant sequence(s) and/or a normal sequence(s). The method of evaluating the efficacy of the drug of the present invention may be useful, for example, in deciding whether the therapeutic strategy for a disease should be shifted so as to increase the dosage of the drug or use another therapeutic agent instead of the drug, based on the detected presence or absence of a mutation(s) and/or the abundance ratio a mutant sequence(s).

Specific examples of a drug to be subjected to the evaluation include a therapeutic agent for gout, a therapeutic agent for hyperuricemia and so on, and especially a therapeutic agent for gout and a therapeutic agent for hyperuricemia.

<Disease Prediction Method>

The disease prediction method of the present invention includes detecting polymorphism in the ABCG2 gene by the above-described polymorphism detection method, and predicting the incidence risk of a disease based on the results of the detection.

According to the method of detecting polymorphism in the ABCG2 gene of the present invention, the presence or absence of a mutation(s) in the ABCG2 gene and the type thereof, particularly the V12M mutation, the Q126X mutation and/or the Q141K mutation, may be detected with a high sensitivity and easily.

Therefore, according to the present invention, prediction of the incidence risk of a disease may be performed based on the detected presence or absence of polymorphism(s). Specifically, the prediction may be carried out by referring to the descriptions in JIKKEN IGAKU (Experimental Medicine), 2010, Vol. 28, No. 8, pp. 1285-1289; British Journal of Clinical Pharmacology, Volume 64, Issue 5, Article first published online: 17 May 2007 or the like with regard to combination of ABCG2 genotypes, a risk of developing a disease and so on.

Specific examples of a disease to be subjected to the prediction include gout, hyperuricemia, porphyria and so on, and especially gout and hyperuricemia.

<Reagent Kit>

The reagent kit of the present invention contains at least one of the probe for detecting polymorphism that is capable of detecting a mutation of the 301st base of the base sequence indicated in SEQ ID NO:1, the probe for detecting polymorphism that is capable of detecting a mutation of the 234th base of the base sequence indicated in SEQ ID NO:2, and the probe for detecting polymorphism that is capable of detecting a mutation of the 161st base of the base sequence indicated in SEQ ID NO:3. This may enable the reagent kit of the present invention to detect polymorphism in the ABCG2 gene.

The reagent kit in the present invention may also contain two or more of the fluorescently labeled oligonucleotides.

In a case where two or more fluorescently labeled oligonucleotides are contained as a probe for detecting polymorphism, the fluorescently labeled oligonucleotides may be contained in a mixed form, or may be independently contained.

The two or more fluorescently labeled oligonucleotides may be labeled with fluorescent dyes whose fluorescence emission wavelengths are different from each other.

By thus using fluorescent dyes whose types are different from each other, the detection with the two or more fluorescently labeled oligonucleotides may also be carried out at the same time even in one reaction system.

In addition, the reagent kit in the present invention may further contain the above-described primer(s) for amplifying a sequence having an ABCG2 gene polymorphism to be detected. This may enable the reagent kit in the present invention to detect polymorphism in the ABCG2 gene with a good accuracy.

With regard to a probe(s) and primer(s) that may be contained in the reagent kit, the above descriptions may be applied as they are.

The reagent kit according to the present invention may contain a reagent by which polymorphism of the 301st base of the base sequence indicated in SEQ ID NO:1 may be detected (301 Detection Reagent). Examples of the reagent include the P1 fluorescently labeled oligonucleotide, and at least one selected from the group consisting of the primers represented by P4 and P5.

The reagent kit according to the present invention may contain a reagent by which polymorphism of the 234th base of the base sequence indicated in SEQ ID NO:2 may be detected (234 Detection Reagent). Examples of the reagent include the P2 fluorescently labeled oligonucleotide, and at least one selected from the group consisting of the primers represented by P6 and P7.

The reagent kit according to the present invention may contain a reagent by which polymorphism of the 161st base of the base sequence indicated in SEQ ID NO:3 may be detected (161 Detection Reagent). Examples of the reagent include the P3 fluorescently labeled oligonucleotide, and at least one selected from the group consisting of the primers represented by P8 and P9.

In regard to the reagent kit according to the present invention, the 301 Detection Reagent, the 234 Detection Reagent and the 161 Detection Reagent may be used individually, or two or more of them may be used in combination.

The P1 fluorescently labeled oligonucleotide may be constituted of an oligonucleotide having a base sequence indicated in SEQ ID NO:4, SEQ ID NO:5, SEQ ID NO:6, SEQ ID NO:7, SEQ ID NO:8 or SEQ ID NO:9, specifically.

The P2 fluorescently labeled oligonucleotide may be constituted of an oligonucleotide having a base sequence indicated in SEQ ID NO:10, SEQ ID NO:11, SEQ ID NO:12, SEQ ID NO:13, SEQ ID NO:14, SEQ ID NO:15, SEQ ID NO:16 or SEQ ID NO:17, specifically.

The P3 fluorescently labeled oligonucleotide may be constituted of an oligonucleotide having a base sequence indicated in SEQ ID NO:18, SEQ ID NO:19, SEQ ID NO:20, SEQ ID NO:21, SEQ ID NO:22 or SEQ ID NO:23, specifically.

In addition to the probe(s) and the primer(s), the reagent kit for detection in the present invention may further include a reagent(s) required for carrying out nucleic acid amplification in the detection method of the present invention, and in particular, a primer(s) for amplification using a DNA polymerase.

In addition, the reagent kit according to the present invention may further include primers for amplifying a base sequence having a region to which the above-described probe can hybridize. With regard to the probe and the primers that may be included in the reagent kit, the above descriptions thereof may be applied as they are.

Besides the probe and the primers, the reagent kit according to the present invention may further include reagents required for carrying out the nucleic acid amplification in the detection method according to the present invention. The probe, the primers and other reagents may be separately contained, or some of them may be contained in the state of a mixture.

The term "separately contained" may refer to a state in which individual reagents are separated from each other such that the non-contact state therebetween is maintained, and does not necessarily require that the individual reagents be contained in separate containers that can be independently handled.

When the reagent kit includes a primer set for amplifying a base sequence including a base at the gene mutation site (a region to which the probe can hybridize), detection of the gene mutation with higher sensitivity, for example, can be achieved.

The reagent kit according to the present invention may further include an instruction manual that describes instructions for the formation of a differential melting curve for a sample containing a nucleic acid to be detected using the ABCG2 probe, and for the detection of a gene mutation in a gene-encoding base sequence through Tm value analysis based on the differential melting curve, or instructions that describes various reagents that are contained, or may additionally be contained, in the reagent kit.

EXAMPLES

The present invention will now be described concretely by way of examples. However, the present invention is not limited to these examples.

Example 1

Example 1-1

Tm Analysis of Single-Stranded Nucleic Acids and Probe

Tm analysis was carried out using a fully-automated SNP analyzer IS-5310 (trade name: I-DENSY (trademark), manufactured by ARKRAY, Inc.) and the reagent for examination of the formulation as shown in Table 11 below.

TABLE 11

| Formulation) (Reaction Solution Volume: 50 µl) 1 × PCR buffer | |
|---|---|
| dNTP | 0.2 mM |
| $MgCl_2$ | 1.5 mM |
| Taq Polymerase (manufactured by ARKRAY, Inc.) | 1.88 U |
| Probe: 5PB-ABCG2 V12M-A-R1 | 0.2 µM |
| Single-Stranded Nucleic Acid | 0.2 µM |

Single-Stranded Nucleic Acid
ABCG2-V12M-50-F-WT
ABCG2-V12M-50-F-mt

The Tm analysis was carried out by performing a reaction at 95° C. for 1 second and 40° C. for 60 seconds, and then measuring the change in the fluorescence intensity over time while raising the temperature from 40° C. to 75° C. at a temperature increasing rate of 1° C. per 3 seconds. The change in the fluorescence intensity derived from the fluorescently labeled probe was measured by using an excitation wavelength in a range from 365 nm to 415 nm and a measurement wavelength in a range from 445 nm to 480 nm.

As a result, it could be confirmed that peaks corresponding to each of Wild Type (in which the 301st base of SEQ ID NO:1 is a G) and Mutant Type (V12M, in which the 301st base of SEQ ID NO:1 is an A) may be detected. The Tm value of Wild Type was 49° C., and the Tm value of Mutant Type was 56° C.

Figure 2A:
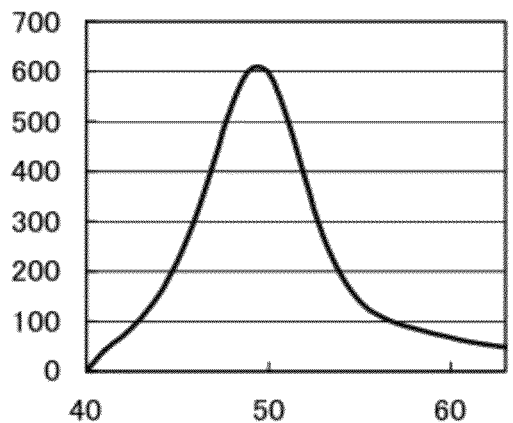
FIG. 2A is melting curves obtained by using the polymorphism detection probe according to Example 1-1 of the present invention.
Figure 2B:
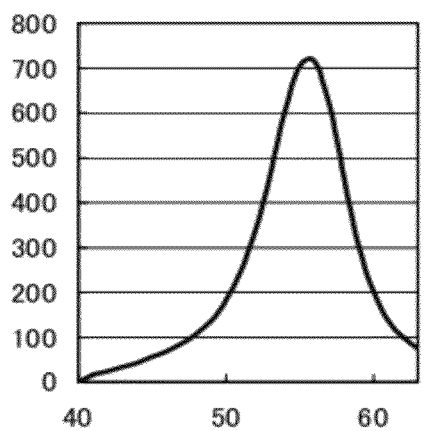
FIG. 2B is melting curves obtained by using the polymorphism detection probe according to Example 1-1 of the present invention.

FIG. 2 shows graphs created from the Tm analysis in cases where Wild Type (A) and Mutant Type (B) were used. The ordinate represents the temperature differential value of the fluorescence intensity, and the abscissa represents the temperature.

Example 1-2

Tm Analysis of Human Genome and Probe

PCR and Tm analysis were carried out using a human genome (manufactured by Roche) as a sample having a mutation to be detected. This human genome was purified from whole blood by a conventional method and used in an amount of 1 μl (100 cp/μl).

The PCR and Tm analysis were carried out using a fully-automated SNP analyzer IS-5310 (trade name: I-DENSY (trademark), manufactured by ARKRAY, Inc.) and the reagent for examination of the formulation as shown in Table 12 below.

The PCR was carried out by performing a reaction at 95° C. for 60 seconds, and then repeating 50 times a cycle of 95° C. for 1 second and 60° C. for 30 seconds.

The Tm analysis was carried out after the PCR by performing a reaction at 95° C. for 1 minute and 40° C. for 60 seconds, and then measuring the change in the fluorescence intensity over time while raising the temperature from 40° C. to 75° C. at a temperature increasing rate of 1° C. per 3 seconds. The change in the fluorescence intensity derived from the fluorescently labeled probe was measured by using an excitation wavelength in a range from 365 nm to 415 nm and a measurement wavelength in a range from 445 nm to 480 nm.

TABLE 12

| Formulation) (Reaction Solution Volume: 50 μl) 1 × PCR buffer | |
|---|---|
| dNTP | 0.2 mM |
| $MgCl_2$ | 1.5 mM |
| Taq Polymerase (manufactured by ARKRAY, Inc.) | 1.88 U |
| ABCG2-V12M-F2 | 1 μM |
| ABCG2-V12M-R1 | 0.5 μM |
| 5PB-ABCG2 V12M-A-R1 | 0.1 μM |
| Purified Human Genome | 1000 copies |

Figure 3:
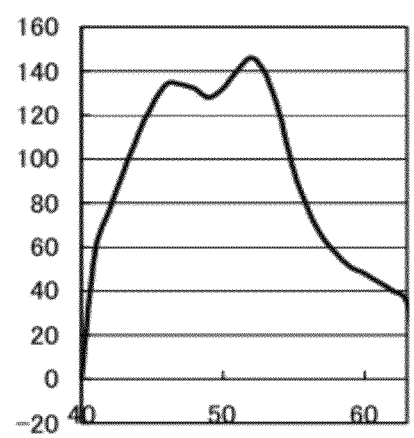
FIG. 3 is a melting curve obtained by using the polymorphism detection probe according to Example 1-2 of the present invention.

As a result, also in case where the human genome purified from whole blood was used as a sample to be detected, it could be confirmed that peaks corresponding to each of Wild Type (in which the 301st base of SEQ ID NO:1 is a G) and Mutant Type (V12M, in which the 301st base of SEQ ID NO:1 is an A) may be detected. The Tm values were 47° C. and 52° C. Graphs created from the Tm analysis are shown in FIG. 3. The ordinate represents the temperature differential value of the fluorescence intensity, and the abscissa represents the temperature.

Details of the probe, primers and single-stranded nucleic acids described above are shown below. The "P" in the probe indicates that the probe is phosphorylated at its 3' end.

TABLE 13

| Name | Sequence | (mer) | SEQ ID NO |
|---|---|---|---|
| Probe | | | |
| 5PB-ABCG2 V12M-A-R1 | (Pacific Blue)-ccttgtgacaTtggga-(P) | 16 | 7 |
| Primer | | | |
| ABCG2-V12M-F2 | gcaatctcatttatctggactatcaacttacta | 33 | 34 |
| ABCG2-V12M-R1 | ttcaggtcattggaagctgtcg | 22 | 35 |
| Single-Stranded Nucleic Acid | | | |
| ABCG2-V12M-50-F-WT | cagtaatgtcgaagttttatcccaGtgtcacaaggaaacaccaatggct | 50 | 24 |
| ABCG2-V12M-50-F-mt | cagtaatgtcgaagttttatcccaAtgtcacaaggaaacaccaatggct | 50 | 25 |

Example 2

Tm analysis was carried out in the same manner as in Example 1-1, except that the single-stranded nucleic acids and the probe shown in Table 14 below were used instead of those in Example 1-1; and, in the Tm analysis, an excitation wavelength in a range from 420 nm to 485 nm and a measurement wavelength in a range from 520 nm to 555 nm were used.

TABLE 14

| Probe | Type | Single-Stranded Nucleic Acid 1 | Single-Stranded Nucleic Acid 2 |
|---|---|---|---|
| 5FL-ABCG2 Q126X-T-RI | Wild Type 1 | ABCG2-Q126X-50-F-WT | |
| | Wild Type 2 | ABCG2-Q126X-40-F-WTC | |
| | Mutant Type 1 | ABCG2-Q126X-50-F-mt | |
| | Mutant Type 2 | ABCG2-Q126X-40-F-mtC | |
| | Mixed Type 1 | ABCG2-Q126X-50-F-WT | ABCG2-Q126X-50-F-mt |
| | Mixed Type 2 | ABCG2-Q126X-40-F-WTC | ABCG2-Q126X-40-F-mtC |
| | Mixed Type 3 | ABCG2-Q126X-50-F-WT | ABCG2-Q126X-40-F-mtC |
| | Mixed Type 4 | ABCG2-Q126X-40-F-WTC | ABCG2-Q126X-50-F-mt |

Details of the probe and single-stranded nucleic acids described above are shown below.

TABLE 15

| Name | Sequence | (mer) | SEQ ID NO |
|---|---|---|---|
| Probe | | | |
| 5FL-ABCG2 Q126X-T-R1 | (FL)-cccactTatacttacttAtaccac-(P) | 24 | 14 |
| Single-Stranded Nucleic Acid | | | |
| ABCG2-Q126X-50-F-WT | caaatgtaattcaggttacgtggtaCaagtaagtatTagtgggtttgcat | 50 | 28 |
| ABCG2-Q126X-50-F-mt | caaatgtaattcaggttacgtggtaTaagtaagtatTagtgggtttgcat | 50 | 29 |
| ABCG2-Q126X-40-F-WTC | ggttaCgtggtaCaagtaagtatCagtgggtttgcattt | 40 | 30 |
| ABCG2-Q126X-40-F-mtC | ggttaCgtggtaTaagtaagtatCagtgggtttgcattt | 40 | 31 |

As a result, it could be confirmed that peaks corresponding to each of Wild Type 1 and Wild Type 2 (in which the 234th base of SEQ ID NO:2 is a G) and Mutant Type 1 and Mutant Type 2 (Q126X, in which the 234th base of SEQ ID NO:2 is a C) may be detected. Further, also in cases where Mixed Type 1, Mixed Type 2, Mixed Type 3 or Mixed Type 4, which is a 1:1 mixture of a wild type of a single-stranded nucleic acid and a mutant type of a single-stranded nucleic acid and is like human genome type, was used, it could be confirmed that each peak may be detected.

The Tm values of Wild Type 1 and Wild Type 2 were both 50° C., and the Tm values of Mutant Type 1 and Mutant Type 2 were both 57° C.

The Tm values of Mixed Type 1 were 50° C. and 56° C.; the Tm values of Mixed Type 2 were 50° C. and 56° C.; the Tm values of Mixed Type 3 were 48° C. and 56° C.; and the Tm values of Mixed Type 4 were 49° C. and 57° C.

FIG. 4 shows graphs created from the Tm analysis in cases where Wild Type 1 (A), Wild Type 2 (C), Mutant Type 1 (B), Mutant Type 2 (D), Mixed Type 1 (E), Mixed Type 2 (F), Mixed Type 3 (G) and Mixed Type 4 (H) were used respectively. The ordinate represents the temperature differential value of the fluorescence intensity, and the abscissa represents the temperature.

Example 3

Tm analysis was carried out in the same manner as in Example 1-1, except that the single-stranded nucleic acids and the probe shown in Table 16 below were used instead of those in Example 1-1; and, in the Tm analysis, an excitation wavelength in a range from 520 nm to 555 nm and a measurement wavelength in a range from 585 nm to 700 nm were used.

TABLE 16

| Probe | Type | Single-Stranded Nucleic Acid 1 | Single-Stranded Nucleic Acid 2 |
|---|---|---|---|
| 3T-ABCG2-mt-R1 | Wild Type | ABCG2-WT-F-40 | — |
| | Mutant Type | ABCG2-mt-F-40 | — |
| | Mixed Type | ABCG2-WT-F-40 | ABCG2-mt-F-40 |

Details of the probe and single-stranded nucleic acids described above are shown below.

TABLE 17

| Name | Sequence | (mer) | SEQ ID NO |
|---|---|---|---|
| Probe | | | |
| 3T-ABCG2-mt-R1 | gctgagaaactTtaagttttc-(TAMRA) | 20 | 21 |

TABLE 17-continued

| Name | Sequence | (mer) | SEQ ID NO |
|---|---|---|---|
| Single-Stranded Nucleic Acid | | | |
| ABCG2-mt-F-40 | acggtgagagaaaacttaAagttctcagcagctcttcggc | 40 | 32 |
| ABCG2-WT-F-40 | acggtgagagaaaacttaCagttctcagcagctcttcggc | 40 | 33 |

As a result, it could be confirmed that peaks corresponding to each of Wild Type (in which the 161st base of SEQ ID NO:3 is a C) and Mutant Type (Q141K, in which the 161st base of SEQ ID NO:2 is an A) may be detected. Further, also in cases where Mixed Type, which is a 1:1 mixture of a wild type of a single-stranded nucleic acid and a mutant type of a single-stranded nucleic acid and is like human genome type, was used, it could be confirmed that each peak may be detected.

The Tm value of Wild Type was 56° C.; the Tm value of Mutant Type was 64° C.; and the Tm values of Mixed Type were 55° C. and 63° C.

Figure 5A:
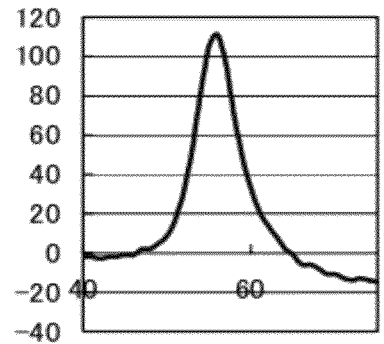
FIG. 5A is melting curves obtained by using the polymorphism detection probe according to Example 3 of the present invention.
Figure 5B:
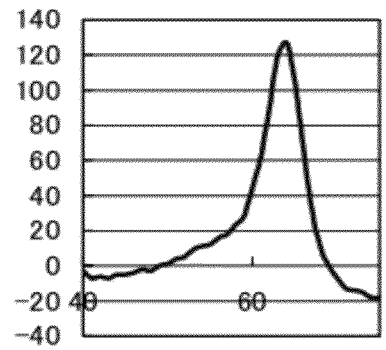
FIG. 5B is melting curves obtained by using the polymorphism detection probe according to Example 3 of the present invention.
Figure 5C:
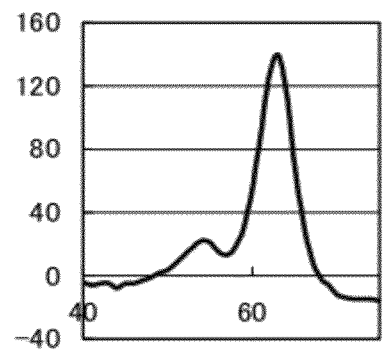
FIG. 5C is melting curves obtained by using the polymorphism detection probe according to Example 3 of the present invention.

FIG. 5 shows graphs created from the Tm analysis in cases where Wild Type (A), Mutant Type (B) and Mixed Type (C) were used. The ordinate represents the temperature differential value of the fluorescence intensity, and the abscissa represents the temperature.

Example 4

Tm analysis was carried out using a fully-automated SNP analyzer IS-5310 (trade name: I-DENSY (trademark), manufactured by ARKRAY, Inc.) and the reagent for examination of the formulation as shown in Table 18 below.

TABLE 18

| Formulation) (Reaction Solution Volume: 50 μl) 1 × PCR buffer | |
|---|---|
| dNTP | 0.2 mM |
| MgCl2 | 1.5 mM |
| Taq Polymerase (manufactured by ARKRAY, Inc.) | 1.88 U |
| ABCG2-F1 | 1 μM |
| ABCG2-R2 | 0.5 μM |
| ABCG2-Q126X-F2 | 1 μM |
| ABCG2-Q126X-R1 | 0.5 μM |
| ABCG2-V12M-F2 | 1 μM |
| ABCG2-V12M-R1 | 0.5 μM |
| 5PB-ABCG2-V12M-A-R1 | 0.2 μM |
| 5FL-ABCG2 Q126X-T-R1 | 0.1 μM |
| 3T-ABCG2-mt-R1 | 0.1 μM |

Details of the primers and probes described above are shown below.

TABLE 19

| Name | Sequence | (mer) | SEQ ID NO |
|---|---|---|---|
| Primer | | | |
| ABCG2-F1 | tgatgttgtgatgggcactctgacg | 25 | 38 |
| ABCG2-R2 | aatgaccctgttaatccgttcg | 22 | 39 |
| ABCG2-Q126X-F2 | gtcttagctgcaaggaaagatccaag | 26 | 36 |
| ABCG2-Q126X-R1 | aaagcacttacccatatagaaacagagg | 28 | 37 |
| ABCG2-V12M-F2 | gcaatctcatttatctggactatcaacttacta | 33 | 34 |
| ABCG2-V12M-R1 | ttcaggtcattggaagctgtcg | 22 | 35 |
| Probe | | | |
| 5PB-ABCG2 V12M-A-R1 | (Pacific Blue)-ccttgtgacaTtggga-(P) | 16 | 7 |
| 5FL-ABCG2 Q126X-T-R1 | (FL)-cccactTatacttacttAtaccac-(P) | 24 | 14 |
| 3T-ABCG2-mt-R1 | gctgagaactTtaagttttc-(TAMRA) | 20 | 21 |

The conditions of the Tm analysis were as follows: a reaction at 95° C. for 1 minute was performed, and then a cycle of 95° C. for 1 second and 60° C. for 30 seconds was repeated 50 times. Thereafter, a reaction at 95° C. for 1 second and 40° C. for 60 seconds was performed, and then the change in the fluorescence intensity over time was measured while raising the temperature from 40° C. to 60° C. at a temperature increasing rate of 1° C. per 3 seconds. The excitation wavelength and the measurement wavelength were, with regard to PACIFIC BLUE, in a range from 365 nm to 415 nm and in a range from 445 nm to 480 nm, respectively; with regard to BODIPY FL, in a range from 420 nm to 485 nm and in a range from 520 nm to 555 nm, respectively; and, with regard to TAMRA, in a range from 520 nm to 555 nm and in a range from 585 nm to 700 nm, respectively. Based on these wavelengths, the change in the fluorescence intensity derived from each fluorescently labeled probe was measured.

Whole blood and purified genome (2000 copies/test) were each used as a template. The method of preparing the whole blood was as follows.

To 70 μl of Diluent 1, 10 μl of whole blood was added, and the resultant was mixed well. Thereafter, 10 μl of the mixture was added to 70 μl of Diluent 2. By heating 17 μl of the resulting mixture at 95° C. for 10 minutes, 4 μl of pretreated whole blood may be obtained. This was used as a template for 1 test.

TABLE 20

| Diluent 1 | |
|---|---|
| Tris-HCl (pH 8.0) | 10 mM |
| EDTA (pH 8.0) | 0.1 mM |
| SDS | 0.30% |

TABLE 21

| Diluent 2 | |
|---|---|
| Tris-HCl (pH 8.0) | 10 mM |
| 500 mM EDTA (pH 8.0) | 0.1 mM |

As a result, in both of the cases where the whole blood was used as a template and the cases where the purified human genome was used, all the peaks corresponding to the V12M mutation, the Q126X mutation or the Q141K mutation could be observed.

In both of the cases of the whole blood and the cases of the purified human genome, the Tm values in cases of the V12M mutation were both 47° C. and 52° C.; the Tm values in cases of the Q126X mutation were both 45° C.; and the Tm values in cases of the Q141K mutation were both 50° C.

Figure 6A:
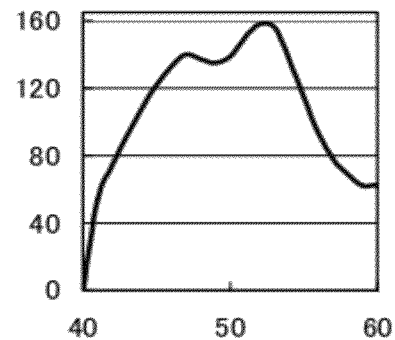
FIG. 6A is melting curves obtained by using the polymorphism detection probes according to Example 4 of the present invention.
Figure 6B:
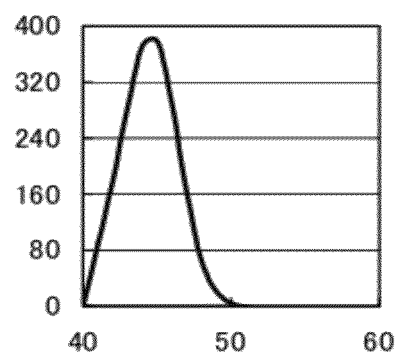
FIG. 6B is melting curves obtained by using the polymorphism detection probes according to Example 4 of the present invention.
Figure 6C:
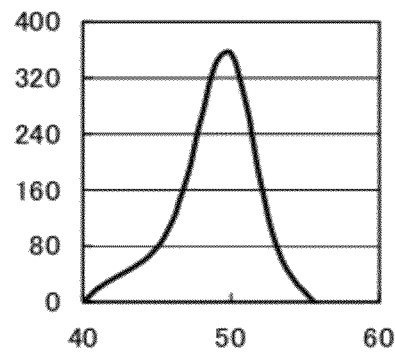
FIG. 6C is melting curves obtained by using the polymorphism detection probes according to Example 4 of the present invention.
Figure 7A:
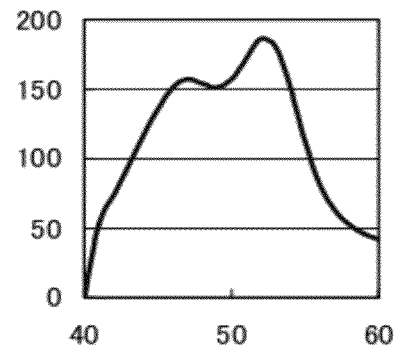
FIG. 7A is melting curves obtained by using the polymorphism detection probes according to Example 4 of the present invention.
Figure 7B:
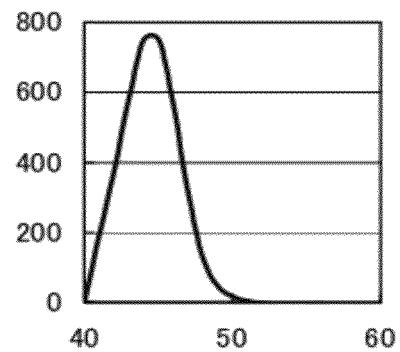
FIG. 7B is melting curves obtained by using the polymorphism detection probes according to Example 4 of the present invention.
Figure 7C:
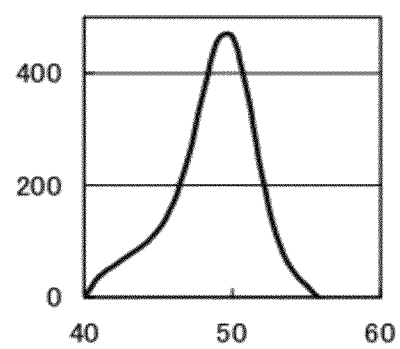
FIG. 7C is melting curves obtained by using the polymorphism detection probes according to Example 4 of the present invention.

FIG. 6 shows graphs created from the Tm analysis in cases of the whole blood (the V12M mutation) (A), the whole blood (the Q126X mutation) (B) and the whole blood (the Q141K mutation) (C); and FIG. 7 shows graphs in cases of the purified human genome (the V12M mutation) (A), the purified human genome (the Q126X mutation) (B) and the purified human genome (the Q141K mutation) (C). The ordinate represents the temperature differential value of the fluorescence intensity, and the abscissa represents the temperature.

Comparative Example 1

Tm analysis was carried out in the same manner as in Example 1-1, except that the probe and the single-stranded nucleic acids shown below were used.

TABLE 22

| Probe | Single-Stranded Nucleic Acid |
|---|---|
| 5PB-ABCG2 V12M-A-F1 | ABCG2-V12M-50-R-WT |
| | ABCG2-V12M-50-R-mt |

Details of the probe and single-stranded nucleic acids described above are as described in Table 23 below.

TABLE 23

| Name | Sequence | (mer) | SEQ ID NO |
|---|---|---|---|
| Probe | | | |
| 5PB-ABCG2 V12M-A-F1 | (Pacific Blue)-cccaAtgtcacaaggaaa-(P) | 18 | 40 |
| Single-Stranded Nucleic Acid | | | |
| ABCG2-V12M-50-R-WT | agccattggtgtttccttgtgacaCtgggataaaaacttcgacattactg | 50 | 26 |
| ABCG2-V12M-50-R-mt | agccattggtgtttccttgtgacaTtgggataaaaacttcgacattactg | 50 | 27 |

As a result, it could be confirmed that peaks corresponding to each of Wild Type (in which the 301st base of SEQ ID NO:1 is a G) and Mutant Type (V12M, in which the 301st base of SEQ ID NO:1 is an A) may be detected. The Tm value of Wild Type was 49° C., and the Tm value of Mutant Type was 57° C.

Figure 8A:
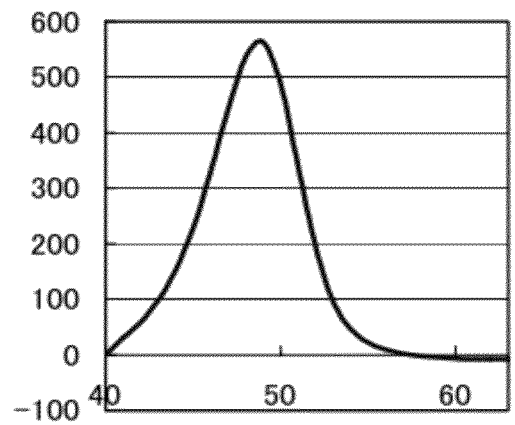
FIG. 8A is melting curves obtained by using the polymorphism detection probe according to Comparative Example 1 of the present invention.
Figure 8B:
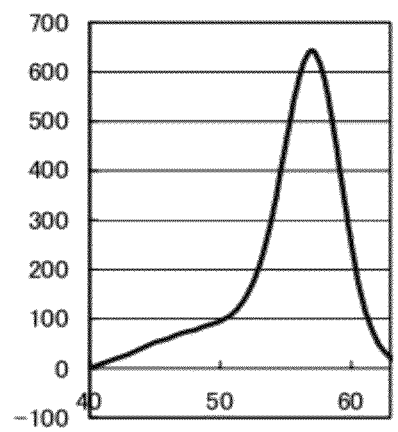
FIG. 8B is melting curves obtained by using the polymorphism detection probe according to Comparative Example 1 of the present invention.

FIG. 8 shows graphs created from the Tm analysis in cases where Wild Type (A) and Mutant Type (B) were used. The ordinate represents the temperature differential value of the fluorescence intensity, and the abscissa represents the temperature.

In addition, Tm analysis of the human genome and the probe was carried out in the same manner as in Example 1-2, except that 5PB-ABCG2 V12M-A-FI was used as a probe instead of 5PB-ABCG2 V12M-A-R1.

As a result, in a case where the human genome purified from whole blood was used as a sample to be detected, the Tm value of Mutant Type could be detected as 55° C., but the Tm value of Wild Type could not be detected.

Figure 9:
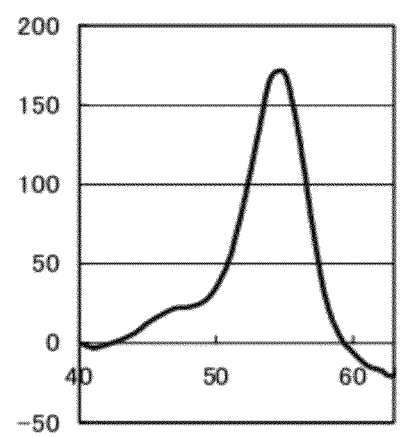
FIG. 9 is a melting curve obtained by using the polymorphism detection probe according to Comparative Example 1 of the present invention.

A graph created from the Tm analysis is shown in FIG. 9. The ordinate represents the temperature differential value of the fluorescence intensity, and the abscissa represents the temperature.

Comparative Example 2

Tm analysis was carried out in the same manner as in Example 2, except that 3FL-ABCG2 Q126X-T-R2 was used as a probe instead of 5FL-ABCG2 Q126X-T-RI in Example 2.

Details of the probe described above are shown below.

TABLE 24

| Name | Probe Sequence | (mer) | SEQ ID NO |
|---|---|---|---|
| 3FL-ABCG2 Q126X-T-R2 | aaacccactCatacttacttAtacc-(FL) | 25 | 41 |

As a result, in cases of Wild Type 1 and Wild Type 2, Mutant Type 2, and Mixed Type 1 to Mixed Type 4, it could be confirmed that each peak may be detected. On the other hand, in case of Mutant Type 1, a pseudo-peak was observed around the Tm value of Wild Type, suggesting the possibility that this might be mistaken for Mixed Type.

The Tm value of Wild Type 1 was 52° C.; the Tm value of Wild Type 2 was 49° C.; the Tm value of Mutant Type 1 was 57° C.; the Tm value of Mutant Type 2 was 56° C.; the Tm values of Mixed Type 1 were 51° C. and 57° C.; the Tm values of Mixed Type 2 were 49° C. and 56° C.; the Tm values of Mixed Type 3 were 51° C. and 56° C.; and the Tm values of Mixed Type 4 were 50° C. and 57° C.

FIG. 10 shows graphs created from the Tm analysis in cases where Wild Type 1 (A), Wild Type 2 (C), Mutant Type 1 (B), Mutant Type 2 (D), Mixed Type 1 (E), Mixed Type 2 (F), Mixed Type 3 (G) and Mixed Type 4 (H) were used respectively. The ordinate represents the temperature differential value of the fluorescence intensity, and the abscissa represents the temperature.

Comparative Example 3

Tm analysis was carried out in the same manner as in Example 3, except that 5T-ABCG2-mt-R2 was used as a probe instead of 3T-ABCG2-mt-R1 in Example 3.

Details of the probe described above are shown below.

TABLE 25

| Name | Sequence | (mer) | SEQ ID NO |
|---|---|---|---|
| 5T-ABCG2-mt-R2 | (TAMRA)-ctgagaactTtaagttttct-(P) | 20 | 42 |

As a result, in all of the case of Wild Type (in which the 161st base of SEQ ID NO:3 is a C), the case of Mutant Type (Q141K, in which the 161st base of SEQ ID NO:2 is an A) and the case of Mixed Type, no peak could be observed.

Figure 11A:
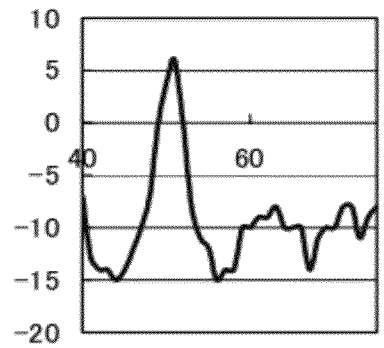
FIG. 11A is melting curves obtained by using the polymorphism detection probe according to Comparative Example 3 of the present invention.
Figure 11B:
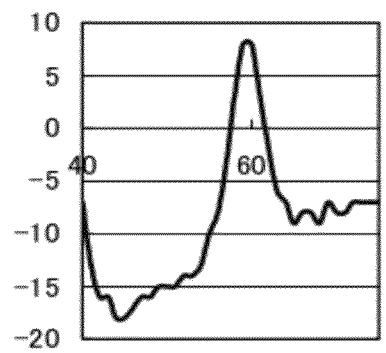
FIG. 11B is melting curves obtained by using the polymorphism detection probe according to Comparative Example 3 of the present invention.
Figure 11C:
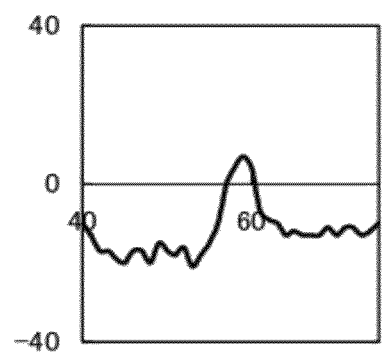
FIG. 11C is melting curves obtained by using the polymorphism detection probe according to Comparative Example 3 of the present invention.

FIG. 11 shows graphs created from the Tm analysis in cases where Wild Type (A), Mutant Type (B) and Mixed Type (C) were used. The ordinate represents the temperature differential value of the fluorescence intensity, and the abscissa represents the temperature.

It was proved from the above that the use of the probes for detecting polymorphism of the present invention may make it possible to detect the V12M mutation, the Q126X mutation and the Q141K mutation among polymorphisms in the ABCG2 gene with a high frequency, may make it possible to detect, using one reagent, plural polymorphisms at the same time and easily, and may fluffier make it possible to detect polymorphisms in the ABCG2 gene directly without purifying whole blood and easily.

What is claimed is:

1. A probe consisting of a fluorescently labeled oligonucleotide selected from the group consisting of
   (i) the fluorescently labeled oligonucleotide consisting of the sequence of SEQ ID NO: 7;
   (ii) the fluorescently labeled oligonucleotide consisting of the sequence of SEQ ID NO: 14; and
   (iii) the fluorescently labeled oligonucleotide consisting of the sequence of SEQ ID NO: 21.

2. The probe according to claim 1, wherein
   the fluorescently labeled oligonucleotide consisting of the sequence of SEQ ID NO: 7 is labeled at its 5' end;
   the fluorescently labeled oligonucleotide consisting of the sequence of SEQ ID NO: 14 is labeled at its 5' end; and
   the fluorescently labeled oligonucleotide consisting of the sequence of SEQ ID NO: 21 is labeled at its 3' end.

3. The probe according to claim 1, wherein a fluorescence intensity at the time when the fluorescently labeled oligonucleotide is hybridized to its target sequence is decreased or increased as compared to the fluorescence intensity at the time when the fluorescently labeled oligonucleotide is not hybridized to its target sequence.

4. The probe according to claim 1, wherein a fluorescence intensity at the time when the fluorescently labeled oligonucleotide is hybridized to its target sequence is decreased as compared to the fluorescence intensity at the time when the fluorescently labeled oligonucleotide is not hybridized to its target sequence.

5. A method of detecting polymorphism in the ABCG2 gene, which comprises
   (I) contacting the probe according to claim 1 and a single-stranded nucleic acid in a sample and hybridizing the fluorescently labeled oligonucleotide and the single-stranded nucleic acid to obtain a hybrid;
   (II) dissociating the hybrid by changing a temperature of the sample containing the hybrid, and measuring a change in a fluorescence signal caused by the dissociation of the hybrid;
   (III) measuring, based on the change in the fluorescence signal, a Tm value which is a temperature at which the hybrid dissociates; and
   (IV) detecting, based on the Tm value, whether polymorphism in the ABCG2 gene on the single-stranded nucleic acid in the sample exists or not.

6. The method of detecting polymorphism of claim 5, which further comprises amplifying the nucleic acid before or simultaneously with the obtaining of the hybrid in (I).

7. A reagent kit, which contains the probe for detecting polymorphism of claim 1.

8. The reagent kit of claim 7, which further contains at least one primer set selected from the group consisting of:
- a primer set for amplifying a region containing a sequence in the base sequence indicated in SEQ ID NO: 1 to which the P1 fluorescently labeled oligonucleotide may hybridize;
- a primer set for amplifying a region containing a sequence in the base sequence indicated in SEQ ID NO: 1 to which the PI' fluorescently labeled oligonucleotide may hybridize;
- a primer set for amplifying a region containing a sequence in the base sequence indicated in SEQ ID NO:2 to which the P2 fluorescently labeled oligonucleotide may hybridize;
- a primer set for amplifying a region containing a sequence in the base sequence indicated in SEQ ID NO:2 to which the P2' fluorescently labeled oligonucleotide may hybridize;
- a primer set for amplifying a region containing a sequence in the base sequence indicated in SEQ ID NO:3 to which the P3 fluorescently labeled oligonucleotide may hybridize; and
- a primer set for amplifying a region containing a sequence in the base sequence indicated in SEQ ID NO:3 to which the P3' fluorescently labeled oligonucleotide may hybridize.

9. A probe set comprising two or three different probes, each of which consists of a fluorescently labeled oligonucleotide selected from the group consisting of
- (i) the fluorescently labeled oligonucleotide consisting of the sequence of SEQ ID NO: 7;
- (ii) the fluorescently labeled oligonucleotide consisting of the sequence of SEQ ID NO: 14; and
- (iii) the fluorescently labeled oligonucleotide consisting of the sequence of SEQ ID NO: 21.

10. The probe set according to claim 9, wherein
the fluorescently labeled oligonucleotide consisting of the sequence of SEQ ID NO: 7 is labeled at its 5' end,
the fluorescently labeled oligonucleotide consisting of the sequence of SEQ ID NO: 14 is labeled at its 5' end, and
the fluorescently labeled oligonucleotide consisting of the sequence of SEQ ID NO: 21 is labeled at its 3' end.

11. A method of detecting polymorphism in the ABCG2 gene, which comprises
- (I) contacting the probe set according to claim 9 and a single-stranded nucleic acid in a sample and hybridizing the fluorescently labeled oligonucleotide and the single-stranded nucleic acid to obtain a hybrid;
- (II) dissociating the hybrid by changing a temperature of the sample containing the hybrid, and measuring a change in a fluorescence signal caused by the dissociation of the hybrid;
- (III) measuring, based on the change in the fluorescence signal, a Tm value which is a temperature at which the hybrid dissociates; and
- (IV) detecting, based on the Tm value, whether polymorphism in the ABCG2 gene on the single-stranded nucleic acid in the sample exists or not.

* * * * *

SEQUENCE LISTING

<160> NUMBER OF SEQ ID NOS: 42

<210> SEQ ID NO 1
<211> LENGTH: 601
<212> TYPE: DNA
<213> ORGANISM: Homo sapiens
<220> FEATURE:
<221> NAME/KEY: variation
<222> LOCATION: (301)..(301)
<223> OTHER INFORMATION: h is a, c or t.

<400> SEQUENCE: 1

```
attaggaccc atttacttat tagggatgta tttgacatct aattggagtt tatgcattcc      60
aagttgtgcc tgtcttccca tttaggtttt taggatgttc ttatcacaat ggtatgggcc     120
attcattgga aatgaagctg ctcattgcca cacatttaaa aatggacttg tttaaatgt      180 attgtcacct agtgtttgca atctcattta tctggactat caacttacta ttgcttttct     240
gtctgcagaa agataaaaac tctccagatg tcttccagta atgtcgaagt ttttatccca     300
htgtcacaag gaaacaccaa tggcttcccc gcgacagctt ccaatgacct gaaggcattt     360
actgaaggag ctgtgttaag ttttcataac atctgctatc gagtaaaact gaagagtggc     420
tttctacctt gtcgaaaacc agttgagaaa gaaatattat cgaatatcaa gtatgtacat     480
gaacttgtaa aaagacagct ttttaattta cctacagtga acctcacagg ttttggctat     540
```

```
ttccaagaaa ctggctatga acattttgt acaagtcttt gcacagatat acagacacat    600
g                                                                    601

<210> SEQ ID NO 2
<211> LENGTH: 480
<212> TYPE: DNA
<213> ORGANISM: Homo sapiens
<220> FEATURE:
<221> NAME/KEY: misc_feature
<222> LOCATION: (234)..(234)
<223> OTHER INFORMATION: n is a, g, c or t.
<220> FEATURE:
<221> NAME/KEY: variation
<222> LOCATION: (245)..(245)
<223> OTHER INFORMATION: w is a or t.

<400> SEQUENCE: 2
agtagaattt ggattcaaag tagccatgag atatatagca tgtgttggag ggaaaaaaac    60
cccacaacat atatattctc ttataggtta ttagacccac aacatatatg tcctcttata   120
ggttattaga tgtcttagct gcaaggaaag atccaagtgg attatctgga gatgttctga   180
taaatggagc accgcgacct gccaatttca aatgtaattc aggttaygtg gtanaagtaa   240
gtatwagtgg gtttgcattt tctgtttcct ctgtttctat atgggtaagt gctttsgctg   300
atagttcaat gtgcttccag ttgattatgt gacatggtcc tagaactgac gttcttaca   360 gcagcttttc ttaatttctc atagacactt atgtgaaaag gcagggagaa tctggaatat   420
ggcccttgta aggacagtga taccaattct agttttgta tcatttctaa aatgatacat    480

<210> SEQ ID NO 3
<211> LENGTH: 341
<212> TYPE: DNA
<213> ORGANISM: Homo sapiens
<220> FEATURE:
<221> NAME/KEY: misc_feature
<222> LOCATION: (161)..(161)
<223> OTHER INFORMATION: n is a, g c or t.

<400> SEQUENCE: 3
gctagaactt taccttagtt atgttatctt tgtggattat gttatgtata ctaaacagtc   60
atggtcttag aaaagactca ttatcattat gtctcattaa aatgctrttt gcctaagga    120 tgatgttgtg atgggcactc tgacggtgag agaaaactta nagttctcag cagctcttcg   180
gcttgcaaca actatgacga atcatgaaaa aaacgaacgg attaacaggg tcattsaaga    240
gttaggtctg gataaagtgg cagactccaa ggtaatgtgg aaaaactgaa agcatcatga   300
tcagcataag taggacttc cctgtgtgga taaaatgact c                         341

<210> SEQ ID NO 4
<211> LENGTH: 50
<212> TYPE: DNA
<213> ORGANISM: Artificial
<220> FEATURE:
<223> OTHER INFORMATION: proble 1-1

<400> SEQUENCE: 4
agccattggt gtttccttgt gacactggga taaaaacttc gacattactg               50

<210> SEQ ID NO 5
<211> LENGTH: 40
<212> TYPE: DNA
<213> ORGANISM: Artificial
<220> FEATURE:
<223> OTHER INFORMATION: probe 1-2
```

```
<400> SEQUENCE: 5
cattggtgtt tccttgtgac actgggataa aaacttcgac                          40

<210> SEQ ID NO 6
<211> LENGTH: 32
<212> TYPE: DNA
<213> ORGANISM: Artificial
<220> FEATURE:
<223> OTHER INFORMATION: probe 1-3

<400> SEQUENCE: 6
ggtgtttcct tgtgacactg ggataaaaac tt                                  32

<210> SEQ ID NO 7
<211> LENGTH: 16
<212> TYPE: DNA
<213> ORGANISM: Artificial
<220> FEATURE:
<223> OTHER INFORMATION: probe 1-4

<400> SEQUENCE: 7
ccttgtgaca ttggga                                                    16

<210> SEQ ID NO 8
<211> LENGTH: 16
<212> TYPE: DNA
<213> ORGANISM: Artificial
<220> FEATURE:
<223> OTHER INFORMATION: probe 1-5

<400> SEQUENCE: 8
ccttgtgaca atggga                                                    16

<210> SEQ ID NO 9
<211> LENGTH: 14
<212> TYPE: DNA
<213> ORGANISM: Artificial
<220> FEATURE:
<223> OTHER INFORMATION: probe 1-6

<400> SEQUENCE: 9
cttgtgacag tggg                                                      14

<210> SEQ ID NO 10
<211> LENGTH: 50
<212> TYPE: DNA
<213> ORGANISM: Artificial
<220> FEATURE:
<223> OTHER INFORMATION: probe 2-1

<400> SEQUENCE: 10
gaaacagagg aaacagaaaa tgcaaaccca ctaatactta cttataccac               50

<210> SEQ ID NO 11
<211> LENGTH: 40
<212> TYPE: DNA
<213> ORGANISM: Artificial
<220> FEATURE:
<223> OTHER INFORMATION: probe 2-2

<400> SEQUENCE: 11
aacccactaa tacttactta taccacgtaa cctgaattac                          40

<210> SEQ ID NO 12
<211> LENGTH: 38
```

-continued

```
<212> TYPE: DNA
<213> ORGANISM: Artificial
<220> FEATURE:
<223> OTHER INFORMATION: probe 2-3

<400> SEQUENCE: 12
cccactaata cttacttata ccacgtaacc tgaattac                              38

<210> SEQ ID NO 13
<211> LENGTH: 34
<212> TYPE: DNA
<213> ORGANISM: Artificial
<220> FEATURE:
<223> OTHER INFORMATION: probe 2-4

<400> SEQUENCE: 13
aacccactaa tacttactta taccacgtaa cctg                                  34

<210> SEQ ID NO 14
<211> LENGTH: 24
<212> TYPE: DNA
<213> ORGANISM: Artificial
<220> FEATURE:
<223> OTHER INFORMATION: probe 2-5

<400> SEQUENCE: 14
cccacttata cttacttata ccac                                             24

<210> SEQ ID NO 15
<211> LENGTH: 24
<212> TYPE: DNA
<213> ORGANISM: Artificial
<220> FEATURE:
<223> OTHER INFORMATION: probe 2-6

<400> SEQUENCE: 15
cccacttata cttacttgta ccac                                             24

<210> SEQ ID NO 16
<211> LENGTH: 12
<212> TYPE: DNA
<213> ORGANISM: Artificial
<220> FEATURE:
<223> OTHER INFORMATION: probe 2-7

<400> SEQUENCE: 16
tacttttacc ac                                                          12

<210> SEQ ID NO 17
<211> LENGTH: 18
<212> TYPE: DNA
<213> ORGANISM: Artificial
<220> FEATURE:
<223> OTHER INFORMATION: probe 2-8

<400> SEQUENCE: 17
tatacttact tctaccac                                                    18

<210> SEQ ID NO 18
<211> LENGTH: 51
<212> TYPE: DNA
<213> ORGANISM: Artificial
<220> FEATURE:
<223> OTHER INFORMATION: probe 3-1

<400> SEQUENCE: 18
ttgcaagccg aagagctgct gagaactgta agttttctct caccgtcaga g               51
```

<210> SEQ ID NO 19
<211> LENGTH: 40
<212> TYPE: DNA
<213> ORGANISM: Artificial
<220> FEATURE:
<223> OTHER INFORMATION: probe 3-2

<400> SEQUENCE: 19
gccgaagagc tgctgagaac tgtaagtttt ctctcaccgt           40

<210> SEQ ID NO 20
<211> LENGTH: 30
<212> TYPE: DNA
<213> ORGANISM: Artificial
<220> FEATURE:
<223> OTHER INFORMATION: probe 3-3

<400> SEQUENCE: 20
gagctgctga gaactgtaag ttttctctca           30

<210> SEQ ID NO 21
<211> LENGTH: 20
<212> TYPE: DNA
<213> ORGANISM: Artificial
<220> FEATURE:
<223> OTHER INFORMATION: probe 3-4

<400> SEQUENCE: 21
gctgagaact ttaagttttc           20

<210> SEQ ID NO 22
<211> LENGTH: 12
<212> TYPE: DNA
<213> ORGANISM: Artificial
<220> FEATURE:
<223> OTHER INFORMATION: probe 3-5

<400> SEQUENCE: 22
ctataagttt tc           12

<210> SEQ ID NO 23
<211> LENGTH: 12
<212> TYPE: DNA
<213> ORGANISM: Artificial
<220> FEATURE:
<223> OTHER INFORMATION: probe 3-6

<400> SEQUENCE: 23
ctctaagttt tc           12

<210> SEQ ID NO 24
<211> LENGTH: 50
<212> TYPE: DNA
<213> ORGANISM: Artificial
<220> FEATURE:
<223> OTHER INFORMATION: template 1-1

<400> SEQUENCE: 24
cagtaatgtc gaagttttta tcccagtgtc acaaggaaac accaatggct           50

<210> SEQ ID NO 25
<211> LENGTH: 50
<212> TYPE: DNA
<213> ORGANISM: Artificial
<220> FEATURE:
<223> OTHER INFORMATION: template 1-2

```
<400> SEQUENCE: 25
cagtaatgtc gaagttttta tcccaatgtc acaaggaaac accaatggct            50

<210> SEQ ID NO 26
<211> LENGTH: 50
<212> TYPE: DNA
<213> ORGANISM: Artificial
<220> FEATURE:
<223> OTHER INFORMATION: template 1-3

<400> SEQUENCE: 26
agccattggt gtttccttgt gacactggga taaaaacttc gacattactg            50

<210> SEQ ID NO 27
<211> LENGTH: 50
<212> TYPE: DNA
<213> ORGANISM: Artificial
<220> FEATURE:
<223> OTHER INFORMATION: template 1-4

<400> SEQUENCE: 27
agccattggt gtttccttgt gacattggga taaaaacttc gacattactg            50

<210> SEQ ID NO 28
<211> LENGTH: 50
<212> TYPE: DNA
<213> ORGANISM: Artificial
<220> FEATURE:
<223> OTHER INFORMATION: template 2-1

<400> SEQUENCE: 28
caaatgtaat tcaggttacg tggtacaagt aagtattagt gggtttgcat            50

<210> SEQ ID NO 29
<211> LENGTH: 50
<212> TYPE: DNA
<213> ORGANISM: Artificial
<220> FEATURE:
<223> OTHER INFORMATION: template 2-2

<400> SEQUENCE: 29
caaatgtaat tcaggttacg tggtataagt aagtattagt gggtttgcat            50

<210> SEQ ID NO 30
<211> LENGTH: 40
<212> TYPE: DNA
<213> ORGANISM: Artificial
<220> FEATURE:
<223> OTHER INFORMATION: template 2-3

<400> SEQUENCE: 30
ggttacgtgg tacaagtaag tatcagtggg tttgcatttt                       40

<210> SEQ ID NO 31
<211> LENGTH: 40
<212> TYPE: DNA
<213> ORGANISM: Artificial
<220> FEATURE:
<223> OTHER INFORMATION: template 2-4

<400> SEQUENCE: 31
ggttacgtgg tataagtaag tatcagtggg tttgcatttt                       40

<210> SEQ ID NO 32
<211> LENGTH: 40
```

```
<212> TYPE: DNA
<213> ORGANISM: Artificial
<220> FEATURE:
<223> OTHER INFORMATION: template 3-1

<400> SEQUENCE: 32
acggtgagag aaaacttaaa gttctcagca gctcttcggc                    40

<210> SEQ ID NO 33
<211> LENGTH: 40
<212> TYPE: DNA
<213> ORGANISM: Artificial
<220> FEATURE:
<223> OTHER INFORMATION: template 3-2

<400> SEQUENCE: 33
acggtgagag aaaacttaca gttctcagca gctcttcggc                    40

<210> SEQ ID NO 34
<211> LENGTH: 33
<212> TYPE: DNA
<213> ORGANISM: Artificial
<220> FEATURE:
<223> OTHER INFORMATION: primer 1-1-F

<400> SEQUENCE: 34
gcaatctcat ttatctggac tatcaactta cta                           33

<210> SEQ ID NO 35
<211> LENGTH: 22
<212> TYPE: DNA
<213> ORGANISM: Artificial
<220> FEATURE:
<223> OTHER INFORMATION: primer 1-1-R

<400> SEQUENCE: 35
ttcaggtcat tggaagctgt cg                                       22

<210> SEQ ID NO 36
<211> LENGTH: 26
<212> TYPE: DNA
<213> ORGANISM: Artificial
<220> FEATURE:
<223> OTHER INFORMATION: primer 2-1-F

<400> SEQUENCE: 36
gtcttagctg caaggaaaga tccaag                                   26

<210> SEQ ID NO 37
<211> LENGTH: 28
<212> TYPE: DNA
<213> ORGANISM: Artificial
<220> FEATURE:
<223> OTHER INFORMATION: primer 2-1-R

<400> SEQUENCE: 37
aaagcactta cccatataga aacagagg                                 28

<210> SEQ ID NO 38
<211> LENGTH: 25
<212> TYPE: DNA
<213> ORGANISM: Artificial
<220> FEATURE:
<223> OTHER INFORMATION: primer 3-1-F

<400> SEQUENCE: 38
tgatgttgtg atgggcactc tgacg                                    25
```

```
<210> SEQ ID NO 39
<211> LENGTH: 22
<212> TYPE: DNA
<213> ORGANISM: Artificial
<220> FEATURE:
<223> OTHER INFORMATION: primer 3-2-R

<400> SEQUENCE: 39
aatgaccctg ttaatccgtt cg                                           22

<210> SEQ ID NO 40
<211> LENGTH: 18
<212> TYPE: DNA
<213> ORGANISM: Artificial
<220> FEATURE:
<223> OTHER INFORMATION: probe X-1

<400> SEQUENCE: 40
cccaatgtca caaggaaa                                                18

<210> SEQ ID NO 41
<211> LENGTH: 25
<212> TYPE: DNA
<213> ORGANISM: Artificial
<220> FEATURE:
<223> OTHER INFORMATION: probe X-2

<400> SEQUENCE: 41
aaacccactc atacttactt atacc                                        25

<210> SEQ ID NO 42
<211> LENGTH: 20
<212> TYPE: DNA
<213> ORGANISM: Artificial
<220> FEATURE:
<223> OTHER INFORMATION: probe X-3

<400> SEQUENCE: 42
ctgagaactt taagttttct                                              20
```